（12) United States Patent
Rosinski

(10) Patent No.: US 12,059,276 B2
(45) Date of Patent: Aug. 13, 2024

(54) SYSTEMS, APPARATUS AND METHODS FOR AUTOMATICALLY COUNTING MEDICAL OBJECTS, ESTIMATING BLOOD LOSS AND/OR COMMUNICATING BETWEEN MEDICAL EQUIPMENT

(71) Applicant: Medline Industries, LP, Northfield, IL (US)

(72) Inventor: Jared Rosinski, Gurnee, IL (US)

(73) Assignee: Medline Industries, LP, Northfield, IL (US)

( * ) Notice: Subject to any disclaimer, the term of this patent is extended or adjusted under 35 U.S.C. 154(b) by 1035 days.

(21) Appl. No.: 16/994,157

(22) Filed: Aug. 14, 2020

(65) Prior Publication Data

US 2021/0052342 A1 Feb. 25, 2021

Related U.S. Application Data

(60) Provisional application No. 62/889,921, filed on Aug. 21, 2019.

(51) Int. Cl.
*A61B 50/37* (2016.01)
*A61B 50/22* (2016.01)
(Continued)

(52) U.S. Cl.
CPC .............. *A61B 50/37* (2016.02); *A61B 50/22* (2016.02); *A61B 90/06* (2016.02); *A61B 90/08* (2016.02);
(Continued)

(58) Field of Classification Search
CPC ...... A61B 2050/375; A61B 2090/0804; A61B 50/37; A61B 50/20; A61B 5/02042
(Continued)

(56) References Cited

U.S. PATENT DOCUMENTS 2,698,270 A 12/1954 Mesek
3,097,649 A 7/1963 Gray
(Continued)

FOREIGN PATENT DOCUMENTS

DE 39178765 12/1990
EP 0948940 10/1999
(Continued)

OTHER PUBLICATIONS

Extended European Search Report from related European Patent Application No. 18805371.4 dated Feb. 18, 2021; 13 pages.
(Continued)

*Primary Examiner* — Paultep Savusdiphol
(74) *Attorney, Agent, or Firm* — Fitch, Even, Tabin & Flannery LLP

(57) ABSTRACT

Many variations of systems, methods and apparatus for counting medical procedure objects, reconciling same, estimating patient blood loss during and/or after a procedure, and/or communicating between medical equipment used in a medical procedure setting are disclosed and/or illustrated herein. More particularly, many systems, methods and apparatus for counting and/or reconciling medical sponges with passive or active tracking devices, properly detecting/estimating blood loss during and/or after a medical procedure to assist with transfusion decision-making and identifying or at least alerting as to post-procedure patient risks, and/or for communicating between devices used during procedures to provide a smart/connected medical procedure environment are disclosed and/or illustrated herein.

5 Claims, 9 Drawing Sheets

(51) Int. Cl.
*A61B 90/00* (2016.01)
*A61B 90/90* (2016.01)
*A61M 5/14* (2006.01)
*G06F 3/048* (2013.01)
*G16H 40/67* (2018.01)
*A61B 50/30* (2016.01)

(52) U.S. Cl.
CPC .............. *A61B 90/39* (2016.02); *A61B 90/90* (2016.02); *A61M 5/1415* (2013.01); *G06F 3/048* (2013.01); *G16H 40/67* (2018.01); *A61B 2050/318* (2016.02); *A61B 2050/375* (2016.02); *A61B 2090/0805* (2016.02); *A61M 2205/35* (2013.01)

(58) Field of Classification Search
USPC ................................................ 235/385, 492
See application file for complete search history.

(56) References Cited

U.S. PATENT DOCUMENTS

| | | | |
|---|---|---|---|
| 3,146,944 A * | 9/1964 | Grippi, Jr. | G06M 7/02 235/98 C |
| 3,367,431 A | 2/1968 | Baker | |
| 3,422,816 A | 1/1969 | Robinson | |
| 3,464,415 A | 9/1969 | Brownlee | |
| 3,587,583 A | 6/1971 | Greenberg | |
| 3,698,393 A | 10/1972 | Stone | |
| 3,749,237 A * | 7/1973 | Dorton | A61B 50/37 206/390 |
| 3,834,390 A | 9/1974 | Hirsch | |
| 3,853,117 A | 12/1974 | Murr | |
| 3,941,132 A | 3/1976 | Lenaghan | |
| 3,965,907 A | 6/1976 | Hardy | |
| 4,075,632 A | 2/1978 | Baldwin | |
| 4,098,728 A | 7/1978 | Rosenblatt | |
| 4,114,601 A | 9/1978 | Abels | |
| 4,193,405 A | 3/1980 | Abels | |
| 4,205,680 A | 6/1980 | Marshall | |
| 4,244,369 A | 1/1981 | McAvinn | |
| 4,264,575 A | 4/1981 | Zimmerman | |
| 4,422,548 A † | 12/1983 | Cheesman | |
| 4,477,256 A | 10/1984 | Hirsch | |
| 4,626,251 A | 12/1986 | Shen | |
| 4,639,253 A | 1/1987 | Dyer | |
| 4,645,499 A | 2/1987 | Rupinskas | |
| 4,658,818 A | 4/1987 | Miller, Jr. | |
| 4,711,996 A | 12/1987 | Drexler | |
| 4,718,897 A | 1/1988 | Elves | |
| 4,739,328 A | 4/1988 | Koelle | |
| 4,832,198 A | 5/1989 | Alikhan | |
| 4,917,694 A | 4/1990 | Jessup | |
| 4,943,939 A | 7/1990 | Hoover | |
| 5,031,642 A | 7/1991 | Nosek | |
| 5,041,103 A | 8/1991 | Rupinskas | |
| 5,045,080 A | 9/1991 | Dyer | |
| 5,049,219 A | 9/1991 | Johns | |
| 5,057,095 A | 10/1991 | Fabian | |
| 5,074,840 A | 12/1991 | Yoon | |
| 5,099,845 A | 3/1992 | Besz | |
| 5,105,829 A | 4/1992 | Fabian | |
| 5,107,862 A | 4/1992 | Fabian | |
| 5,112,325 A | 5/1992 | Zachry | |
| 5,188,126 A | 2/1993 | Fabian | |
| 5,211,129 A | 5/1993 | Taylor | |
| 5,231,273 A | 7/1993 | Caswell | |
| 5,300,922 A | 4/1994 | Stoffer | |
| 5,329,944 A | 7/1994 | Fabian | |
| 5,374,813 A | 12/1994 | Shipp | |
| 5,443,082 A | 8/1995 | Mewburn | |
| 5,456,718 A | 10/1995 | Szymaitis | |
| 5,463,376 A | 10/1995 | Stoffer | |
| 5,541,604 A | 7/1996 | Meier | |
| 5,610,811 A | 3/1997 | Honda | |
| 5,629,498 A | 5/1997 | Pollock | |
| 5,637,850 A | 6/1997 | Honda | |
| 5,650,596 A | 7/1997 | Morris | |
| 5,664,582 A | 9/1997 | Szymaitis | |
| 5,678,569 A | 10/1997 | Chew | |
| 5,681,862 A | 10/1997 | Hollis | |
| 5,805,451 A | 9/1998 | Speas | |
| 5,833,603 A | 11/1998 | Kovacs | |
| 5,923,001 A † | 7/1999 | Morris | |
| 5,931,824 A | 8/1999 | Stewart | |
| 5,944,023 A | 8/1999 | Johnson | |
| 5,991,728 A | 11/1999 | Debusk | |
| 6,009,878 A | 1/2000 | Weijand | |
| 6,026,818 A | 2/2000 | Blair | |
| 6,076,007 A | 6/2000 | England | |
| 6,223,137 B1 | 4/2001 | McCay | |
| 6,272,368 B1 | 8/2001 | Alexandrescu | |
| 6,305,381 B1 | 10/2001 | Weijand | |
| 6,366,206 B1 | 4/2002 | Ishikawa | |
| 6,607,170 B1 * | 8/2003 | Hoftman | A61B 50/37 206/370 |
| 6,777,623 B2 | 8/2004 | Ballard | |
| 6,861,954 B2 | 3/2005 | Levin | |
| 6,998,541 B2 | 2/2006 | Morris | |
| 7,019,650 B2 | 3/2006 | Volpi | |
| 7,118,029 B2 | 3/2006 | Nycz | |
| 7,135,978 B2 | 11/2006 | Gisselberg | |
| 7,158,030 B2 | 1/2007 | Chung | |
| 7,158,754 B2 | 1/2007 | Anderson | |
| 7,180,014 B2 | 2/2007 | Farber | |
| 7,256,696 B2 | 8/2007 | Levin | |
| 7,268,684 B2 | 9/2007 | Tethrake | |
| 7,297,834 B1 | 11/2007 | Shapiro | |
| D557,421 S | 12/2007 | Fleck | |
| 7,307,530 B2 | 12/2007 | Fabian | |
| 7,411,506 B2 | 1/2008 | Volpi | |
| 7,399,899 B2 | 7/2008 | Fabian | |
| 7,420,468 B2 | 9/2008 | Fabian | |
| 7,464,713 B2 | 12/2008 | Fabian | |
| 7,518,502 B2 | 4/2009 | Austin | |
| 7,530,967 B2 | 5/2009 | Brown | |
| 7,541,933 B2 | 6/2009 | Volpi | |
| 7,557,710 B2 | 7/2009 | Sanchez | |
| 7,557,711 B2 | 7/2009 | Volpi | |
| 7,589,634 B2 | 9/2009 | Frank | |
| 7,696,877 B2 | 4/2010 | Barnes | |
| 7,703,674 B2 | 4/2010 | Stewart | |
| 7,774,244 B2 | 8/2010 | Kreiner | |
| 7,787,931 B2 | 8/2010 | Fabian | |
| 7,795,491 B2 | 9/2010 | Stewart | |
| D631,152 S | 1/2011 | Hampton | |
| 7,893,840 B2 | 2/2011 | Volpi | |
| D634,004 S | 3/2011 | Hampton | |
| D636,871 S | 4/2011 | Hampton | |
| 8,063,760 B2 | 11/2011 | Volpi | |
| 8,105,296 B2 | 1/2012 | Morris | |
| 8,279,068 B2 | 4/2012 | Morris | |
| 8,181,860 B2 | 5/2012 | Fleck | |
| 8,193,938 B2 | 6/2012 | Halberthal | |
| 8,479,989 B2 | 1/2013 | Fleck | |
| 8,576,076 B2 | 1/2013 | Morris | |
| 8,428,517 B2 | 4/2013 | Ting | |
| 8,544,660 B2 | 10/2013 | Foley | |
| 8,554,579 B2 | 10/2013 | Tribble | |
| 8,710,957 B2 | 4/2014 | Blair | |
| 8,792,693 B2 | 7/2014 | Satish | |
| 8,872,662 B2 | 10/2014 | Halberthal | |
| 8,897,523 B2 | 11/2014 | Satish | |
| 8,978,229 B2 | 3/2015 | Halberthal | |
| 8,983,167 B2 | 3/2015 | Satish | |
| 8,985,446 B2 | 3/2015 | Fleck | |
| 9,019,078 B2 | 4/2015 | Hamelin | |
| 9,035,748 B2 | 5/2015 | Greefkes | |
| 9,047,663 B2 | 6/2015 | Satish | |
| 9,070,270 B2 | 6/2015 | Kreiner | |
| 9,168,104 B2 | 10/2015 | Dein | |
| 9,171,368 B2 | 10/2015 | Satish | |
| 9,198,727 B1 * | 12/2015 | Samuels | A61F 15/001 |
| 9,289,943 B2 | 3/2016 | Halberthal | |

(56) References Cited

U.S. PATENT DOCUMENTS

| | | |
|---|---|---|
| 9,471,820 B2 | 10/2016 | Arthaber |
| 9,474,693 B2 | 10/2016 | Ranalletta |
| 9,507,981 B2 | 11/2016 | Dor |
| 9,662,273 B2 | 2/2017 | Ranalletta |
| 9,595,104 B2 | 3/2017 | Satish |
| 9,646,375 B2 | 5/2017 | Satish |
| 9,652,655 B2 | 5/2017 | Satish |
| 9,773,320 B2 | 9/2017 | Satish |
| 9,824,441 B2 | 11/2017 | Satish |
| 9,870,625 B2 | 1/2018 | Satish |
| 9,936,906 B2 | 4/2018 | Satish |
| 10,002,269 B2 | 6/2018 | Dor |
| 10,154,885 B1 | 12/2018 | Barnett |
| 10,282,839 B2 | 5/2019 | Satish |
| 10,424,060 B2 | 9/2019 | Satish |
| 10,426,356 B2 | 10/2019 | Satish |
| 10,528,782 B2 | 1/2020 | Satish |
| 10,555,675 B2 | 2/2020 | Satish |
| 10,641,644 B2 | 5/2020 | Satish |
| 10,706,541 B2 | 7/2020 | Satish |
| 10,719,747 B2 | 7/2020 | Stewart |
| 10,789,710 B2 | 9/2020 | Satish |
| 10,863,933 B2 | 12/2020 | Satish |
| 10,905,521 B2 | 2/2021 | Stewart |
| 10,957,179 B2 | 3/2021 | Satish |
| 11,009,600 B2 | 5/2021 | Shoarinejad |
| 11,109,941 B2 | 9/2021 | Kumar |
| 2002/0049650 A1 | 4/2002 | Reff |
| 2002/0090930 A1 | 7/2002 | Fujiwara |
| 2003/0105394 A1 | 6/2003 | Fabian |
| 2003/0224996 A1 | 12/2003 | Opperman |
| 2004/0077546 A1 | 4/2004 | Oppermann |
| 2004/0169587 A1 | 9/2004 | Washington |
| 2005/0038556 A1 | 2/2005 | Gagnon |
| 2005/0075564 A1 | 4/2005 | Ballard |
| 2005/0255141 A1 | 11/2005 | Oppermann |
| 2006/0029591 A1 | 2/2006 | Vukicevic |
| 2006/0044137 A1 | 3/2006 | Morris |
| 2006/0065739 A1 | 3/2006 | Falls |
| 2006/0140464 A1 | 6/2006 | Feilkas |
| 2006/0241396 A1 | 10/2006 | Fabian |
| 2006/0241399 A1 | 10/2006 | Fabian |
| 2006/0256081 A1 | 11/2006 | Zalewski |
| 2006/0264260 A1 | 11/2006 | Zalewski |
| 2006/0282873 A1 | 12/2006 | Zalewski |
| 2006/0287086 A1 | 12/2006 | Zalewski |
| 2006/0287087 A1 | 12/2006 | Zalewski |
| 2007/0015558 A1 | 1/2007 | Zalewski |
| 2007/0015559 A1 | 1/2007 | Zalewski |
| 2007/0083170 A1 | 4/2007 | Stewart |
| 2007/0094303 A1 | 4/2007 | Zwingenberger |
| 2007/0103313 A1 | 5/2007 | Washington |
| 2007/0125392 A1 | 6/2007 | Olson, Jr. |
| 2007/0166353 A1 | 7/2007 | Oppermann |
| 2007/0268133 A1 | 11/2007 | Sanchez |
| 2007/0285249 A1 | 12/2007 | Blair |
| 2008/0043901 A1 | 2/2008 | Maschke |
| 2008/0051746 A1 | 2/2008 | Shen-Gunther |
| 2008/0096654 A1 | 4/2008 | Mondesir |
| 2008/0098448 A1 | 4/2008 | Mondesir |
| 2008/0100825 A1 | 5/2008 | Zalewski |
| 2008/0138289 A1 | 6/2008 | Goronkin |
| 2008/0174409 A1 | 7/2008 | Frank |
| 2008/0204245 A1 | 8/2008 | Blair |
| 2008/0233170 A1 | 9/2008 | Oppermann |
| 2008/0237341 A1† | 10/2008 | Fleck |
| 2008/0269597 A1 | 10/2008 | Benetti |
| 2008/0272913 A1 | 11/2008 | Barnes |
| 2009/0014518 A1 | 1/2009 | Stewart |
| 2009/0317002 A1 | 12/2009 | Dein |
| 2010/0010372 A1 | 1/2010 | Brown |
| 2010/0074883 A9 | 3/2010 | Vukicevic |
| 2010/0090901 A1 | 4/2010 | Smith |
| 2010/0132600 A1 | 6/2010 | Dean |
| 2010/0160865 A1 | 6/2010 | Zeltzer |
| 2010/0191107 A1 | 7/2010 | Bowers |
| 2010/0258632 A1 | 10/2010 | Good |
| 2010/0305714 A1 | 12/2010 | Procter |
| 2011/0174877 A1 | 7/2011 | Fleck |
| 2011/0306899 A1 | 12/2011 | Brown |
| 2012/0062365 A1 | 3/2012 | Hansen |
| 2012/0075464 A1 | 3/2012 | Derenne |
| 2012/0095422 A1* | 4/2012 | Morris ............... A61M 1/777 340/10.1 |
| 2012/0132600 A1* | 5/2012 | Foley ................. A61B 50/10 211/85.15 |
| 2012/0146789 A1 | 6/2012 | De Luca |
| 2013/0021192 A1 | 1/2013 | Daly |
| 2013/0037663 A1 | 2/2013 | Walther |
| 2013/0149294 A1 | 6/2013 | Rueger |
| 2013/0186413 A1 | 7/2013 | Haines |
| 2013/0301901 A1 | 11/2013 | Satish |
| 2014/0021087 A1 | 1/2014 | Adler |
| 2014/0055618 A1 | 2/2014 | Myers |
| 2014/0126788 A1 | 5/2014 | Satish |
| 2014/0128838 A1 | 5/2014 | Satish |
| 2014/0243770 A1 | 8/2014 | Stewart |
| 2014/0261457 A1 | 9/2014 | Lother |
| 2014/0262553 A1* | 9/2014 | Pollock ............... B65F 1/1415 177/1 |
| 2015/0109442 A1 | 4/2015 | Derenne |
| 2015/0164603 A1 | 6/2015 | Fleck |
| 2015/0168207 A1* | 6/2015 | Pollock ............... G01G 19/414 177/1 |
| 2015/0193127 A1 | 7/2015 | Chai |
| 2015/0261291 A1 | 9/2015 | Mikhailov |
| 2015/0273102 A1 | 10/2015 | Hissink |
| 2015/0280649 A1 | 10/2015 | Nero, Jr. |
| 2015/0342745 A1 | 12/2015 | Roux |
| 2015/0363618 A1 | 12/2015 | Fleck |
| 2016/0008091 A1* | 1/2016 | Saotome ............. A61B 90/90 340/572.1 |
| 2016/0045276 A1* | 2/2016 | Pfanner .............. A61B 90/94 235/385 |
| 2016/0045279 A1 | 2/2016 | Daon |
| 2016/0051418 A1 | 2/2016 | Fleck |
| 2016/0065909 A1 | 3/2016 | Derenne |
| 2016/0070942 A1 | 3/2016 | Dor |
| 2016/0085922 A1* | 3/2016 | Sweeney ............. A61B 90/90 705/2 |
| 2016/0171262 A1 | 6/2016 | Fleck |
| 2016/0212577 A1 | 7/2016 | Dor |
| 2016/0379504 A1* | 12/2016 | Bailey ................ G06V 40/20 434/219 |
| 2017/0143429 A1 | 5/2017 | Richmond |
| 2017/0151386 A1 | 6/2017 | Walther |
| 2017/0184442 A1 | 6/2017 | Satish |
| 2017/0224437 A1 | 8/2017 | Fleck |
| 2017/0258547 A1* | 9/2017 | Karasina ............. A61B 50/24 |
| 2017/0296301 A1 | 10/2017 | Dor |
| 2018/0068179 A1 | 3/2018 | Derenne |
| 2018/0204103 A1 | 7/2018 | Dor |
| 2018/0227547 A1 | 8/2018 | Derenne |
| 2018/0243044 A1 | 8/2018 | Fleck |
| 2018/0266870 A1* | 9/2018 | Lin ..................... G01G 17/04 |
| 2018/0285704 A1 | 10/2018 | Stewart |
| 2018/0303570 A1* | 10/2018 | Dreosso ............. A61B 50/13 |
| 2018/0338801 A1 | 11/2018 | Barnett |
| 2018/0344429 A1 | 12/2018 | Stewart |
| 2018/0353256 A1 | 12/2018 | Stewart |
| 2019/0000589 A1 | 1/2019 | Vanderwoude |
| 2019/0235069 A1 | 8/2019 | Shaorinejad |
| 2019/0244707 A1 | 8/2019 | Becker |
| 2019/0349554 A1 | 11/2019 | Derenne |
| 2019/0388183 A1* | 12/2019 | Poirier .............. G16H 40/20 |
| 2020/0143190 A1 | 5/2020 | Hastings |
| 2020/0315732 A1 | 10/2020 | Fleck |
| 2020/0320359 A1 | 10/2020 | Stewart |
| 2021/0019672 A1 | 1/2021 | Paramasivan |
| 2021/0085428 A1 | 3/2021 | Yavari |
| 2021/0128270 A1 | 5/2021 | Stewart |

(56) References Cited

U.S. PATENT DOCUMENTS

| | | | |
|---|---|---|---|
| 2021/0259800 A1 | 8/2021 | Fleck | |
| 2022/0296332 A1* | 9/2022 | Satish | A61B 90/361 |

FOREIGN PATENT DOCUMENTS

| | | |
|---|---|---|
| EP | 1219259 | 7/2002 |
| EP | 1610704 A1 | 1/2006 |
| WO | 9422580 | 10/1994 |
| WO | 199527252 | 10/1995 |
| WO | 199745057 | 12/1997 |
| WO | 9830166 | 7/1998 |
| WO | 2004086997 | 10/2004 |
| WO | 2014165740 | 10/2014 |
| WO | 2015017044 | 2/2015 |
| WO | 2016176187 | 11/2016 |
| WO | 2017112051 | 6/2017 |
| WO | 2018217396 | 11/2018 |

OTHER PUBLICATIONS

Third Party Submission Under 37 CFR 1.290 for U.S. Appl. No. 16/815,925 dated Nov. 24, 2021.

Clearcount Medical Solutions, Inc., "The SmartSponge System Operating Procedures Manual", Jan. 31, 2006, 54 pp.

Haldor Advanced Technologies Ltd., 510(k) Summary (21 CFR 807.92) ORLocateTM System, Aug. 12, 2010, 7 pp.

Haldor Advanced Technologies, ORLocate Sponge Solution Product Information Sheet, 2017, 2 pp.

Patent Cooperation Treaty, International Searching Authority, Notification of Transmittal of the International Search Report and the Written Opinion of the International Searching Authority, or the Declaration, issued in International Application No. PCT/US2020/022380 dated Jul. 7, 2020, 169 pp.

Patent Cooperation Treaty, International Searching Authority, Notification of Transmittal of the International Search Report and the Written Opinion of the International Searching Authority, or the Declaration, issued in International Patent Application No. PCT/US2018/029556 dated Aug. 10, 2018; 17 pages.

U.S. Food & Drug Administration, 510(k) Premarket Notification, https://accessdata.fda.gov/scripts/cdrh/cfdocs/cfpmn.cfm?ID=K100551, Mar. 27, 2018, 3 pp.

\* cited by examiner
† cited by third party

SYSTEMS, APPARATUS AND METHODS FOR AUTOMATICALLY COUNTING MEDICAL OBJECTS, ESTIMATING BLOOD LOSS AND/OR COMMUNICATING BETWEEN MEDICAL EQUIPMENT

CROSS-REFERENCE TO RELATED APPLICATIONS

This application claims benefit to U.S. Provisional Application No. 62/889,921, filed Aug. 21, 2019, and is incorporated herein by reference in its entirety.

FIELD

This invention relates generally to systems, methods and apparatus for counting medical procedure objects, reconciling same, estimating patient blood loss during and/or after a procedure and/or communicating between medical equipment used in a medical procedure setting, and, more particularly, to systems, methods and apparatus for counting and/or reconciling medical sponges with passive or active tracking devices, properly detecting and/or estimating blood loss during and/or after a medical procedure to assist with transfusion decision-making and identifying or at least alerting as to post-procedure patient risks, and/or for communicating between devices used during procedures to provide a smart/connected medical procedure environment.

BACKGROUND

Medical procedures have evolved over time into very efficient and well-choreographed routines, often using pre-packaged surgical kits containing all instruments and equipment needed for the particular procedure at hand. However, these routines often involve numerous medical personnel working with a litany of different instruments, often times in a relatively small or cramped space for clinical settings and vast open spaces for operating room settings. In such procedures and environments, one of the most difficult things to do is track all items being used during the procedure to make sure all are accounted for at the end of the procedure and tracking how much blood loss (estimated blood loss or EBL) the patient has had during the procedure in order to determine how much blood the patient needs. Monitoring EBL is important for both transfusion decision-making and predicting postoperative hemoglobin (Hb) levels. For example, postoperative Hb levels are important because too low of an Hb level could lead to anemia which can eventually lead to adverse cerebrovascular outcomes (e.g., stroke, particularly in cardiac procedures) and can identify hemorrhaging concerns such as post-partum hemorrhaging in obstetrics which can lead to hemorrhagic shock and organ failure.

Conventional systems exist for detecting the amount of blood loss a patient has had during a procedure or EBL. Originally, this was done by physician assessment based on a review of the amount of blood absorbed by sponges or vacuum suction systems. This proved to be rather unreliable given that irrigation fluids like saline, other bodily fluids, tissues and other foreign particles would often mix with the recovered blood thereby distorting the actual measurement of blood subjectively taken by the physician. An improved method of detecting blood loss called gravimetric analysis involved weighing blood-soaked sponges and reducing that weight by the weight of a dry sponge. This technique assumed 1 mL of blood equals 1 gram and, thus, when the weight of the sponge prior to its use is subtracted from the weight of the blood-soaked sponge, one could roughly determine the amount of blood lost. However, this process proved somewhat unreliable as well for the same reasons as the physician's assessment (or eye-balling) process described above (e.g., additional fluids, tissues and other items could be present beyond blood thereby giving an inaccurate assessment of blood loss). Yet another improved method was developed called photometric analysis (or assay analysis) which used rinsing techniques for the collected fluids and using spectrophotometry and intraoperative laboratory work-ups of the samples to determine hemoglobin concentration. While this technique has proven to be far more reliable, it is also a very laborious process, time consuming and costly. Thus, while it is a preferred approach, it is rarely used in practice.

A newer tablet computer application has been developed to simplify this process using computer vision algorithms and feature extraction technology to assess hemoglobin ("Hb") concentration contained in surgical sponges through photographic analysis. The system is called Triton by Gauss Surgical and operates by first taking images of the sponges or suction canisters, then pre-processes these to isolate the sponge surface and the blood-containing portions within the sponge and the canister fluids. Then the software normalizes the images to minimize the effects of fluctuations in ambient lighting for the images. Next, the software extracts a set of geometric and pixel-level features and utilized a proprietary mathematical model that maps clusters of these features to known Hb mass values (accounting for variations in the fluid such as saline, bodily fluid, tissues, etc.) to come up with an amount of blood lost during the procedure. The tablet has a front facing camera and is mounted to the intravenous ("IV") pole so that surgical sponges can be photographed live or intra-operatively (meaning during the procedure). The user has to take the picture of each sponge and suction canister used in the procedure, and can do so either using the tablet's touch screen or using a Bluetooth-connected foot pedal accessory. A Bluetooth-connected scale is also used to weigh the sponges as well. The images and data are then stored both on the tablet and on a remote server for processing after the procedure is completed/closed-out. This system has been shown to be very similar in performance to the photometric analysis method and superior with respect to the gravimetric method, however, it still requires the user to perform additional tasks in utilizing the tablet to photograph the sponges and requires additional equipment beyond the conventional sponge rack.

With respect to tracking or reconciling items used during a procedure, numerous systems exist for tracking and/or counting/reconciling such items during a procedure and prior to its conclusion or close-out. For example, conventional systems exist to count surgical sponges that are used during a procedure, such as laparotomy (or lap) sponges, and to estimate how much blood the patient has lost during the procedure via those items. The Applicant has a sponge rack system (e.g., Medline NON50511) that hangs from an IV pole and suspends a bag with a series of individual sponge compartments, which those involved in a procedure can use to bag sponges as they are removed from a patient to keep track of the sponges during the procedure. Other smart sponge systems exist that track how many sponges have been used during a procedure, how many have been returned or discarded, and how many remain out and unaccounted for during or after a procedure. Often these systems are blind, passive systems that simply note when an item is unaccounted for and require medical personnel to use equipment, such as scanners to scan items being checked-out for use or in for return, and then items, such as wands with integral antennas, to waive over a medical procedure area (e.g., over a patient, over surrounding patient support surfaces (like bedding, gurneys, tables, etc.), surrounding equipment, personnel, waste receptacles, etc.) to locate the unaccounted for item. This takes up valuable time and does not provide the medical personnel with any additional information that would be helpful in locating the unaccounted-for item.

Often, these systems are also limited to a particular item (e.g., a sponge instead of other items/instruments used) and/or only track a small portion of a medical procedure area (e.g., around the sponge scanning system itself, etc.). For example, some smart sponge systems consist of a cart that includes a waste receptacle or bucket and track the sponges as used in the procedure. Such systems limit their product tracking to sponges alone and ignore the numerous other items/instruments utilized during a procedure (e.g., scalpels, scissors, tongs, gauze, mesh, suture needles, etc.). They also only track what is checked out and what is returned to the receptacle and do not track the surrounding procedure area. As mentioned above, they provide an antenna wand to search the surrounding procedure area that is not being tracked, but that requires medical personnel to perform additional tasks and does not confirm for the personnel if they are using the equipment appropriately.

Some conventional systems go beyond tracking sponges and offer counting or reconciliation features as well, but these systems often require medical personnel to apply machine readable labels on all items that are to be tracked, which is again labor intensive and adds more work for medical personnel, rather than reduces the steps they have to perform so they can focus on the procedure at hand and do so efficiently to make the best use of what often is very expensive high-tech operating room time. These systems often include interrogators that communicate with a base command unit to track a location of an object that has been marked with a machine-readable label so that the item can be tracked, but often this involves having the user scan via a scanner each item when checked out and then returned and then use a mobile wand antenna to scan for missing items. Less intelligent versions of such systems are also employed that simply use metal detection technology to detect if any item has been left behind in sensitive areas, however, conventional procedural arenas (e.g., clinics, operating rooms, etc.) are so inundated with metal objects, it is hard to use metal detection technology effectively and/or conveniently for such purposes.

Even in instances where medical kits are provided with pre-marked or pre-labeled items so that they can be tracked easier, these systems limit the tracking to those items in the kit and not additional items that may need to be employed during a procedure. In such systems, the focus is again on tracking a limited number of items and the procedural area, and again, the system operates blind either simply notifying personnel of a missing item or requiring personnel to scan surrounding area to locate the missing item. No further information is provided to the user to ensure they are properly performing their intended task.

Another problem associated with conventional systems is that they do not "talk" or communicate with one another or share data between one another. They also do not automate some of the steps currently required of medical personnel which would otherwise help the personnel perform their tasks more quickly and efficiently. Given the expense associated with each minute of operating room time, such inefficiencies become extremely costly over time. Still further, conventional systems often are provided as stand-alone proprietary systems which take-up more space than is desired in any procedural setting yielding a more congested and less integrated work environment.

Accordingly, it has been determined that a need exists for systems, methods and apparatus for overcoming the aforementioned shortcomings and improving medical procedures and medical procedure management, and, more particularly, to systems, methods and apparatus for counting sponges and/or detecting blood loss during and/or after medical procedures, and assisting medical personnel with the procedure.

BRIEF DESCRIPTION OF THE FIGURES

Embodiments of the invention are illustrated in the figures of the accompanying drawings in which.

Elements in the figures are illustrated for simplicity and clarity and have not necessarily been drawn to scale or to include all features, options or attachments. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. Similarly, while distinct embodiments are discussed it should be understood that features from one embodiment may be combined with features of other embodiments in order to develop yet further embodiments and such further embodiments are contemplated herein. The terms and expressions used herein have the ordinary technical meaning as is accorded to such terms and expressions by persons skilled in the technical field as set forth above except where different specific meanings have otherwise been set forth herein.

DESCRIPTION OF THE INVENTION

Many variations of systems, methods and apparatus for counting medical procedure objects, reconciling same, estimating patient blood loss during and/or after a procedure, and/or communicating between medical equipment used in a medical procedure setting are disclosed and/or illustrated herein. More particularly, many systems, methods and apparatus for counting and/or reconciling medical sponges with passive or active tracking devices, properly detecting/estimating blood loss during and/or after a medical procedure to assist with transfusion decision-making and identifying or at least alerting as to post-procedure patient risks, and/or for communicating between devices used during procedures to provide a smart/connected medical procedure environment are disclosed and/or illustrated herein.

Figure 1:
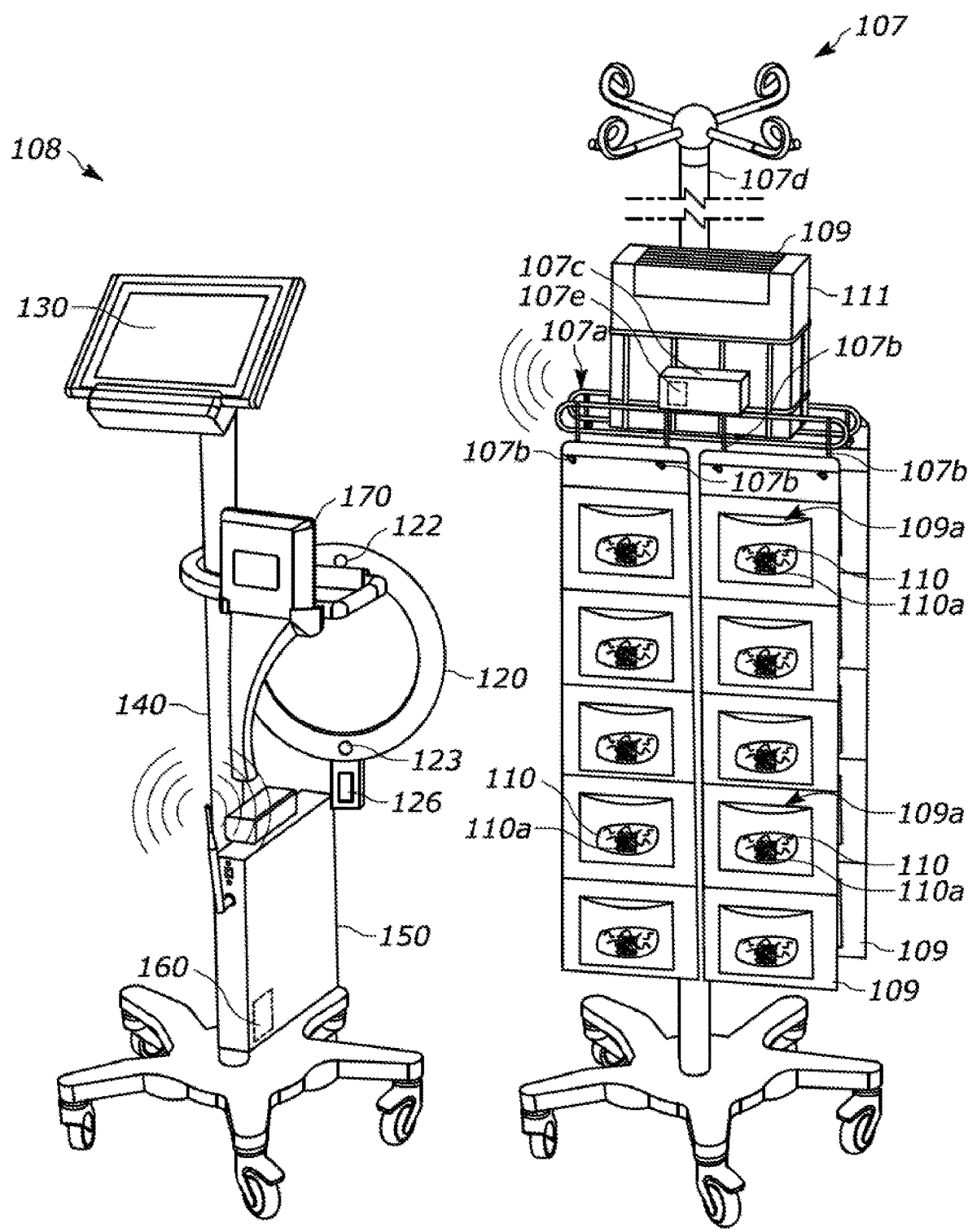
FIG. 1 is a perspective view of a medical object counting system (e.g., sponge counting system) that communicates with a medical object reconciliation system in accordance with features of the invention.

For example, turning to FIG. 1, there is illustrated a system 107 for counting medical sponges, and a system 108 for reconciling medical procedure objects used during a procedure (e.g., to ensure nothing is left behind and/or locate any items that may be missing, lost or misplaced). In a preferred form, the sponge counting rack system 107 detects sponges 110 by a computer detectable tag, such as RFID or RF tag 110a, when the sponge 110 is brought within a read range of the system 107. As will be discussed further below, in some forms, the sponge counting system 107 may confirm all sponges are accounted for to the medical personnel involved in the procedure and/or alert when a missing sponge is detected. In other forms it may communicate data relating to one or both of these instances (e.g., all sponges accounted for or one or more sponges missing) to a remote device so that the medical personnel involved in the procedure are alerted to this data at the remote device. In the form shown in FIG. 1, the remote device is the reconciling system 108 and the sponge counting system 107 communicates the sponge data to the reconciling system 108 so that the medical personnel involved in the procedure need only look to that device 108 to determine if any sponges are unaccounted for or missing.

In the form shown, the sponge counting system or sponge counter rack 107 includes a body 107a having a plurality of supports 107b for suspending at least one sponge counting bag, e.g., bags 109, for use during a medical procedure. The at least one sponge counting bag 109 having a plurality of pockets 109a for storing used sponges 110. In the form shown, the pockets 109a are sized for individual sponges 110 so that a visual count can also be performed by the medical personnel involved in the procedure (or user) as a redundant check to confirm no sponges 110 have gone unaccounted for at the conclusion of a procedure. Further, the sponge detector 107c may be part of a passive or active tracking device.

In FIG. 1, the sponge counter rack 107 further including a sponge detector 107c for detecting the used sponges 110 as they are disposed in the plurality of pockets during a medical procedure on a patient. In a preferred form, the sponge detector is an electronic detector that detects the presence of the used sponges as they are placed either in the plurality of pockets 109a or within a read range of the electronic detector 107c. In one form, the electronic detector 107c is an active device that is self-powered and energizes one or more passive devices located on the used sponges 110, e.g., tags 110a, when the used sponges 110 are brought within a read-range of the electronic detector 107c to register the presence of the used sponge 110. In alternate forms, the electronic detector 107c may be a passive device that is energized by one or more active devices located on the used sponges 110 when the used sponges 110 are brought within a read-range of the electronic detector 107c to register the presence of the used sponge. However, due to the active device needing an energy source it is preferred to make the detector 107c the active device and the tags 110a on sponges 110 the passive devices.

In a preferred form, the electronic detector 107c is an RF or RFID reader which detects the presence of an RF or RFID tag 110a located on the used sponge 110 to register the presence of the used sponge 110 at the sponge counter rack 107. In the form shown, the RF or RFID detector 107c may include an internal antenna within its housing. However, in alternate forms, the detector 107c may utilize an external antenna for detecting the presence of sponges 110 within the read range of the detector 107c. As will be discussed in further detail below with respect to FIGS. 2 and 3, in alternate forms, the external antenna may hang from the housing of detector 107c, or it may be attached to or integrated with another portion of the sponge counting rack 107 (e.g., such as being a linear antenna attached to or embedded in an intravenous (IV) pole 107d that the sponge counter rack 107 is connected to, or being attached to or embedded in an accessory to the IV pole, such as a radial antenna connected to a wheel-type handle for an IV pole, etc.).

In FIG. 1, the body 107a supports a container 111 of stored sponge counting bags 109 in a dispensable position so that sponge counting bags 109 may be dispensed from the container 111 and suspended from the plurality of supports 107b. In the form shown, the sponge counter rack 107 is configured to suspend two sponge bags 109 on each side of the sponge counter rack 107 and positions the dispensing container 111 containing either a roll of sponge bags 109 or folded stack of sponge bags 109 above the dispensed or un-stored sponge bags 109 when the dispensed or un-stored sponge bags are suspended from supports 107b. The sponge counter rack body 107a is attachable to a conventional IV pole 107d and positionable along the length of the pole 107d as desired by the user (e.g., taller users may position the body 107a higher on the IV pole 107d, shorter users may position the body 107a lower on the IV pole 107d, etc.). In a preferred form, the body 107a will be positioned low enough on the IV pole 107d such that the hangers located at the top of the IV pole 107d may still be used for other equipment during the medical procedure if desired, yet the suspended or un-stored sponge bags 109 will not drag on the ground or interfere with the wheels/casters of the mobile base of the IV pole 107d.

Figure 5:
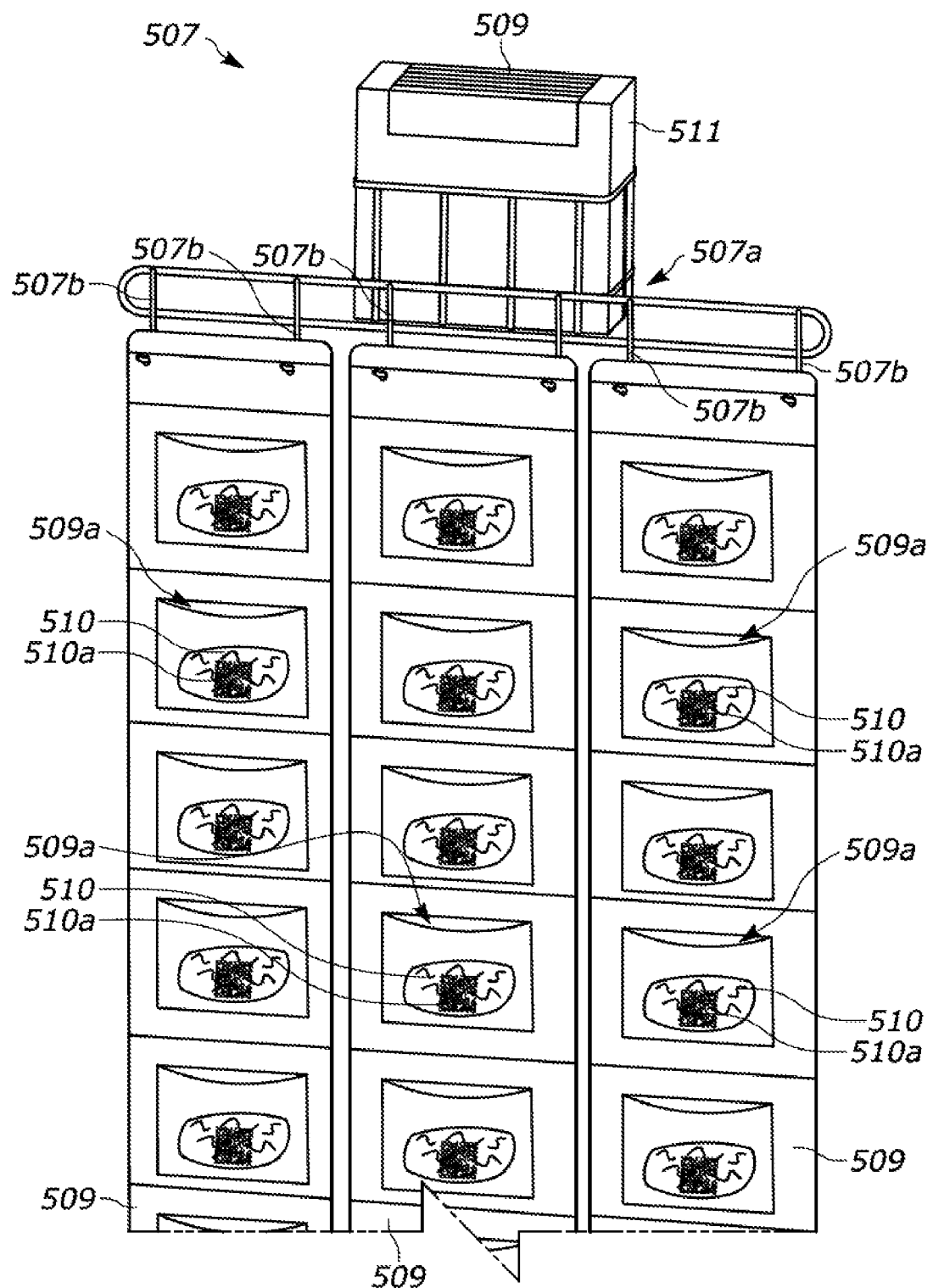
FIG. 5 is a partial perspective view of another medical object counting system in accordance with other features of the invention and illustrating a sponge rack capable of supporting more than two columns of sponge bags.

While container 111 is shown as having a rectangular shape with a tear-off portion exposing the folded sponge bags 109 stored therein, it should be understood that in alternate forms, the container 111 may take a variety of shapes such as a cylinder that dispenses the sponge bags 109 from a surface thereof (e.g., like a wipes dispenser). It should also be understood that while body 107a is shown as being mountable to a conventional IV pole 107d, in other forms it may be configured to mount to a top of a conventional IV pole 107d or the sponge counting rack 107 may itself have its own support surface rather than using a conventional IV pole 107d. For example, in alternate forms, the body 107a may be configured for wall-mounting rather than mounting on a pole 107d as is shown in FIG. 5. In a preferred form, the body 107a will be configured to allow for either pole mounting or wall mounting.

In the form shown in FIG. 1, the sponge counter rack 107 further includes a communication module or circuit 107e for communicating to a remote device data relating to the used sponges 110. In a preferred form, the communication circuit 107e and electronic detector 107c are integrated into a module that can be connected to and removed from at least one of the smart sponge counter rack body 107a or a conventional IV pole 107d, and the communication circuit 107e allows the system 107 to communicate to a remote device via any conventional communication technique (e.g., wireless fidelity (Wi-Fi), Cellular, radio frequency (RF), infrared (IR), Bluetooth (BT), Bluetooth Low Energy (BLE), Zigbee, near field communication (NFC), etc.). In one form, the communication circuit 107e serves as a network interface and allows the sponge counter rack 107 to communicate with any remote device that is also connected to the network, such as reconciliation system 108.

In the form shown in FIG. 1, sponge counter rack 107 is configured to only engage in one-way communication with the remote device, e.g., reconciliation system 108. As an example, one form of remote device may be reconciliation system 108. In the form shown, the reconciliation system 108 includes at least one wand 120, a controller 126, and a system interface 130. Users of these components may thus use the system interface 130 to interact with reconciliation system 108 and may at least obtain sponge rack information from system 107 via system interface 130. In a preferred form, the user will actually be able to interact with both the reconciliation system 108 and sponge counter rack 107 as will be discussed further with other embodiments.

In the form shown in FIG. 1, the reconciliation system 108 is provided in cart form with mobile cart 140 and includes a network interface or connection 150 and memory 160 for storing data obtained by the reconciliation system 108 and/or sponge counter rack 107. The wand 120 will preferably include a sensor for determining when the wand is capable of properly scanning the target area. In the form shown, such a sensor is at least one of a proximity sensor 122 and/or a motion sensor, such as accelerometer 123, along with a controller 126 in electronic communication with one or more of these sensors 122, 123. Thus, when a procedure is about to conclude or has concluded, or when the user has been notified that a medical device or object is missing, the user may remove wand 120 from cart 140 and scan the patient to ensure no medical objects or devices have been left behind, (e.g., that no retained objects exist with the patient). The controller 126 will use the proximity sensor 122 to ensure the wand is being held within the appropriate proximity to the target being scanned and the accelerometer 123 to ensure the wand is not being moved at too fast or too slow a speed or with an improper orientation in relation to the target being scanned in order to ensure that a proper scan is done with wand 120.

The proximity sensor 122 may be any type of conventional proximity sensor capable of identifying when the wand 120 is within the desired scanning range of a target area. For example, the proximity sensor may be one or more of an optical proximity sensor, an ultrasonic proximity sensor, a sonar proximity sensor, a radar proximity sensor, a capacitive proximity sensor, an inductive proximity sensor, a doppler proximity sensor, a magnetic proximity sensor (e.g., a Hall effect proximity sensor, etc.). In some forms, the proximity sensor may include one or more components located only on the wand 120. While in other forms a more complex proximity sensor may be used including at least one component located on wand 120 and at least a second component located on or proximate the target area to be scanned (e.g., the patient drapes or covers may include or be lined with an item serving as the second component that interacts with the first component to provide proximity data).

The motion sensor 123 may be an accelerometer (or accelerometers), and is used to detect the speed and/or orientation with which the wand is being moved to detect and warn if the user is moving the wand too fast or holding it in an improper orientation in order to properly scan the target area (e.g., patient, surrounding area, receptacles, etc.). The accelerometers 123 may be of the two-axis or three-axis type to detect two-dimensional (2D) or three-dimensional (3D) movement of the wand, respectively. In a preferred form, the accelerometers 123 will be three-axis, 3D accelerometers so that 3D movement of the wand 120 can be detected and monitored.

With the data the accelerometers 123 provide, the system 108 can determine if the wand 120 is moving too fast to properly scan the target area or if it is oriented in a way that is not appropriate or preferred for scanning the target area (e.g., held at too angled or tilted of a position). In one form, the system 108 is setup to accept zero to six seconds (0 s-6 s) per pass as an acceptable speed with which to wand the target area. In another form, however, the system 108 will be setup to accept zero to three seconds (0 s-3 s) per pass as an acceptable speed and will alert the user if the wand 120 is being moved faster than that speed. If desired, the range can be set to an even lower tolerance (e.g., 0 s-2 s) per pass. In a preferred form, the wand system will be configured such that the target speed threshold of the wand can be adjusted to allow customization for different intended uses or workflows (e.g., allowing the user to set one speed for a torso procedure, another speed for a knee procedure, etc.). In still other forms, the system will allow customization to account for the size of the patient being scanned as well. For example, in a preferred form, the system will be configured with a distance buffer that is used to ensure proper scan penetration. Thus, for more petite patients, the wand may be held at a further distance from the patient and still have enough penetration to satisfy the distance buffer set for the wand. However, in other instances where a much larger patient is being scanned, the system may be set to require the wand be held closer to the patient in order to ensure sufficient scan penetration to satisfy the distance buffer requirements of the system.

In a preferred form, the wand scan will take 30-40 seconds (30 s-40 s), however, in alternate arrangements it may be twenty to 60 seconds (20 s-60 s). A reason for the speed control and/or orientation positioning control is to ensure that the wand is not in an undesirable state for detecting any items from a procedure to minimize the risk that an item could be left behind. As for orientation, it is desirable to keep the wand 120 perpendicular to the target area being scanned. In one form, a zero to thirty degrees (0°-30°) tolerance may be maintained. In other forms, the tolerance may be tighter, such as zero to twenty degrees (0°-20°) from perpendicular. In still other forms, the motion sensor may also include a gyroscope to assist with detecting rotational movement of the wand or, more likely, a combination of both accelerometer and gyroscope. For example, in procedures involving implants such as a knee transplant, it may be desirable to also detect the rotational movement of the wand to ensure the user has appropriately wanded around the entire knee completely before confirming the procedure can conclude.

Numerous different types of motion sensors may be used for wand 120 so long as they convey the desired wand parameters to determine if the wand 120 is sufficiently positioned to scan the target area. For example, any one of the following motion sensing controllers may be used, including: U.S. Patent Application Publication No. 20150261291A1, published Sep. 17, 2015, entitled "Methods and systems tracking head mounted display (HMD) and calibrations for HMD headband adjustments"; U.S. Patent Application Publication No. 20060256081A1, published Nov. 16, 2006, entitled "Scheme for detecting and tracking user manipulation of a game controller body"; U.S. Patent Application Publication No. 20060287086A1, published Dec. 21, 2006, entitled "Scheme for translating movements of a hand-held controller into inputs for a system"; U.S. Patent Application Publication No. 20060264260A1, published Nov. 23, 2006, entitled "Detectable and trackable hand-held controller"; U.S. Patent Application Publication No. 20060287087, published Dec. 21, 2006, entitled "Method for mapping movements of a hand-held controller to game commands"; U.S. Patent Application Publication No. 20070015559A1, published Jan. 18, 2007, entitled "Method and apparatus for use in determining lack of user activity in relation to a system"; U.S. Patent Application Publication No. 20070015558A1, published Jan. 18, 2007, entitled "Method and apparatus for use in determining an activity level of a user in relation to a system"; U.S. Patent Application Publication No. 20060282873A1, published Dec. 14, 2006, entitled "Hand-held controller having detectable elements for tracking purposes"; U.S. Patent Application Publication No. 20080100825A1, published May 1, 2008, entitled "Mapping movements of a hand-held controller to the two-dimensional image plane of a display screen"; U.S. Patent Application Publication No. 20080098448A1, published Apr. 24, 2008, entitled "Controller configured to track user's level of anxiety and other mental and physical attributes"; and U.S. Patent Application Publication No. 20080096654A1, published Apr. 24, 2008, entitled "Game control using three-dimensional motions of controller" the entire disclosures of which are all incorporated herein by reference in their entirety.

In some forms, the system may be provided with a single sensor (e.g., a proximity sensor 122 or a motion sensor 123), however, in a preferred form, the system will include both a proximity sensor 122 and a motion sensor 123 in order to assist the user in confirming when the system is used in the appropriate way (as will be discussed in FIG. 9 below). It should be understood, however, that features of one embodiment discussed herein may be combined with features of other embodiments herein to create numerous other embodiments, and all are contemplated to be covered by the disclosure herein. In a preferred form, the wand 120 will be setup to consider being within sixteen inches (16") of the target area to be scanned as being within the proper read range, traveling at a speed equal to or less than three seconds (<3 sec.) per pass of the target to be a proper scan speed and being perpendicular or ninety degrees to the target area for scanning plus or minus thirty degrees (90°±30°) to be a proper wand orientation. These parameters are merely exemplary and may be altered depending on system setup and/or intended use.

In some forms, an indicator will also be provided to further relay this wand information to the user of the wand as will be discussed further with respect to the embodiment of FIGS. 6 and 7). For example, a visual display with one or more lights (e.g., red and green LEDs) to confirm proper use or alert to improper use (e.g., green LED illuminated when being used properly, red LED illuminated when not being used property such as either too far away from target, being moved too fast in relation to target or being held in an improper orientation such as not generally square to target, etc.). The indicator may also (or alternatively) include haptic feedback so as to physically indicate to a user of the wand these same things (e.g., not within proper proximity/read range, traveling too fast, not held at the proper orientation, etc.). The reconciliation system 108 may further include a scanner 170 for users to scan in and out medical objects being used during the medical procedure to keep track of same and/or alert of potentially missing items. In the form shown in FIG. 1, the scanner 170 is positioned on cart 140 to make it convenient to scan items in and out with scanner 170 without the need to remove the scanner 170 from cart 140, however, in a preferred form, the scanner 170 is removable from cart 140 to allow for scanning remote from the cart 140 if desired. These and other features of a smart wand reconciliation system are disclosed in U.S. Patent Application No. 62/817,151, filed Mar. 12, 2019, and entitled Systems, Apparatus and Methods for Properly Locating Items which is incorporated herein by reference in its entirety.

Conventional reconciliation systems exist currently in the industry and include a variety of different wand configurations for detecting retained objects or, more particularly, the RFID tags on the medical instruments or objects used during the procedure. See, for example, the following U.S. patents issued to Haldor Advanced Technologies Ltd. including: U.S. Pat. No. 8,193,938B2 issued Jun. 5, 2012 and entitled "Apparatus for Identifying and Tracking Multiple Tools and Disposables", U.S. Pat. No. 8,872,662B2 issued Oct. 28, 2014 and entitled "Antenna, Apparatus and Method for Identifying and Tracking Multiple Items", U.S. Pat. No. 8,978,229B2 issued Mar. 17, 2015 and entitled "Device and Method for Attaching a Tag to a Tool" and U.S. Ser. No. 10/002,269B2 issued Jun. 19, 2018 and entitled "Mobile Handheld Antenna for Reading Tags", all of which are incorporated herein by reference in their entirety. In general, these wand systems include an antenna in the wand that detects tags placed on items used during the procedure so that the items may be found prior to the conclusion of the procedure and not left behind (particularly not left in the patient, such as in a patient cavity). The tags may be active (meaning they contain their own power source to transmit a signal) or passive (meaning they use the power emitted by the wand antenna to energize and transmit a signal), however, in most cases passive RFID tags are used due to the disposable nature of many of the items used in medical procedures. The signals received from the tags are transferred to a multiplexer which multiplexes the signals and transfers them to a reader to identify the unique identifier associated with each tag which the controller uses to determine what instrument (e.g., sponge, gauze, scalpel, scissors, clamp, etc.) has been detected by that unique identifier. In conventional systems the proper scanning range is typically within twenty inches (i.e., between 0"-20"), which is referred to as the "read range" of the wand. Some even have a smaller read range of between zero and sixteen inches (0"-16") or even zero and fourteen inches (0"-14"). These systems, however, fail to include features that allow a user to confirm if the wand 120 is within the desired scanning range of the target area to be scanned (e.g., within the read range of the wand) and thus can result in a user missing a retained object if the user 106 is not holding the wand 120 within the proper scanning range of the target area or read range. Given the speed at which medical staff are asked to work during procedures, it is feasible that personnel using a wand can inadvertently let the wand travel outside of the intended read range while scanning an area and/or patient which can ultimately lead to missed retained objects because the wand was too far away to pick-up the RFID tag.

Figure 2:
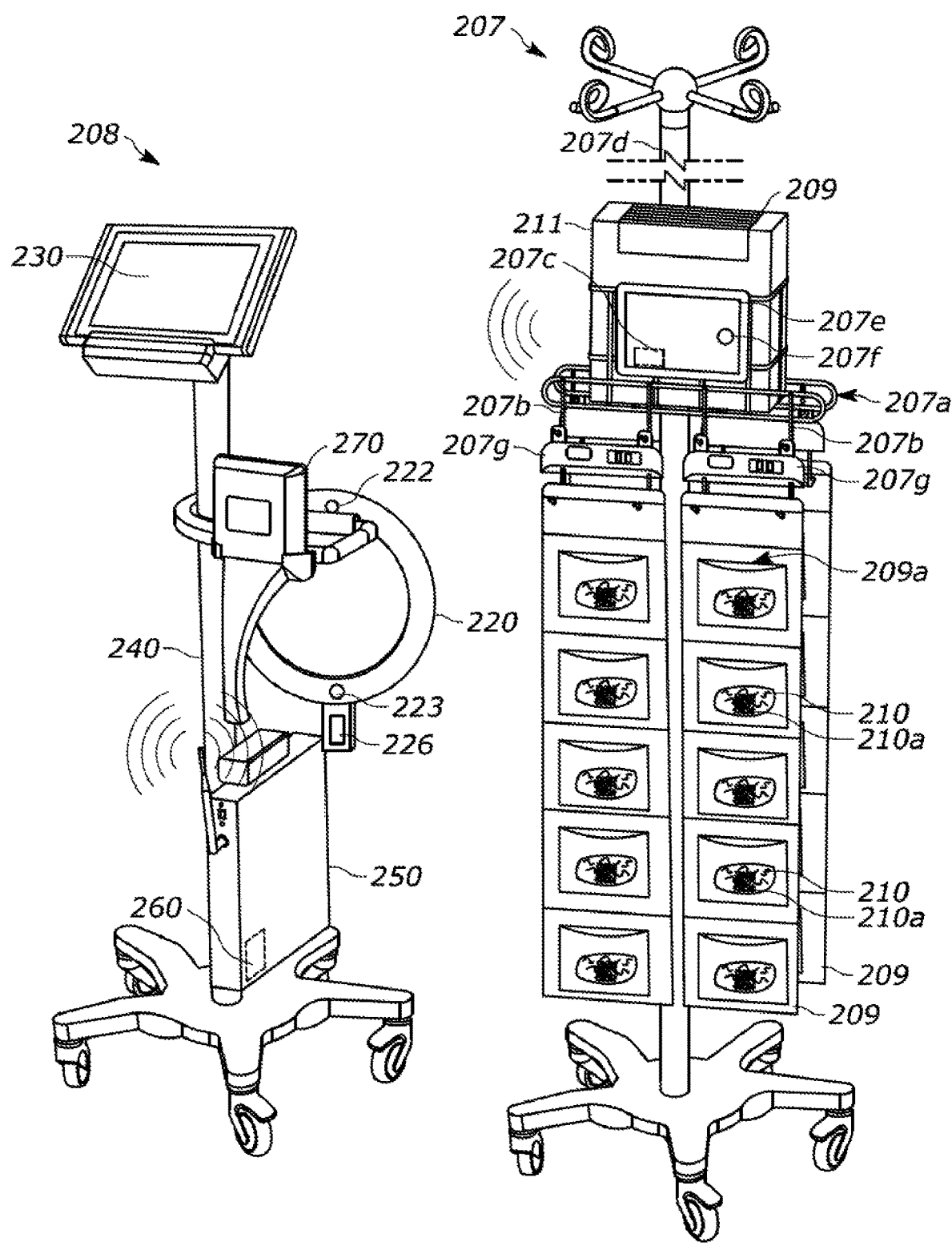
FIG. 2 is a perspective view of an alternate medical object counting system with estimated blood loss (EBL) and/or hemoglobin (Hb) detection capabilities and a medical object reconciliation system in accordance with other features of the invention.

In the form shown in FIG. 1, the sponge counter rack 107 engages in one-way communication with the reconciliation system 108 and the user uses the reconciliation system interface 130 to read the data provided by both the sponge counter rack 107 and reconciliation system 108. In a preferred form, the interface 130 is a tablet that is removable from cart 140 in order to give the user flexibility to position and use the tablet interface 130 where desired throughout the procedure. It should be understood, however, that in alternate embodiments, the sponge counter rack 107 may be configured to allow two-way communications between the sponge counter rack 107 and any remote device in electronic communication with the sponge counter rack 107. For example, while the embodiment of FIG. 1 illustrates a sponge counter rack 107 that the user does not interact with beyond dispensing and hanging sponge bags 109 and removing same from supports 107b, in alternate forms, the sponge counter rack 107 may be configured with its own interface that a user may use to interact with the sponge counter rack 107. An example of such an embodiment is illustrated in FIG. 2. For convenience, items that are similar to those discussed above with respect to the embodiment of FIG. 1 will use the same latter two-digit reference numeral but begin with the prefix "2" to simply distinguish one embodiment from the other. Thus, in FIG. 2 the sponge counter rack and reconciliation systems will be referenced by reference numerals 207 and 208, respectively.

In FIG. 2, the sponge counter rack 207 includes a similar body 207a defining a receptacle for container 211 for dispensing dispensable sponge bags 209 with each bag 209 having a plurality of pockets 209a for receiving/storing used sponges after a medical procedure. The body 207a further having a plurality of supports 207b for suspending bags 209 from body 207a and being mountable to a conventional IV pole 207d such that the dispensed or in-use bags may be suspended at a desired height while still remaining off the floor and out of the way of the wheels or castors for IV pole 207d. While the body 207a shown is in the form of a wire-frame structure, it should be understood that alternate body configurations may be utilized such as plastic molded bodies, metal solid-form bodies, etc., and the plurality of supports 207b may either be integrally formed with the body as is shown in FIGS. 1-2, or alternatively may be discrete structures connected to the body 207.

Unlike the prior embodiment of FIG. 1, however, the sponge bag counter rack 207 further includes an interface 207e which not only allows the system 207 to communicate data relating to the detected sponges 210, but also allows the user to interact with the system 207. For example, in one form, interface 207e is a tablet computer with touch screen display and graphical user interface (GUI) which the user may use to interact with the interface 207e. In a preferred form, interface 2073 will also include a camera 207f for capturing pictures of the used sponges 210 as they are passed by the interface 207e and eventually stored in pockets 209a of bags 209. The tablet 207e may be configured to communicate with remote devices or a network in any of the manners discussed above, but preferably will utilize Wi-Fi and/or Bluetooth communications (e.g., including without limitation BLE) to communicate with other items on the network or within Bluetooth range.

In addition, sponge counter rack system 207 also includes scales 207g for weighing the sponge bags 209 suspended from the body 207a and the used sponges 210 disposed within the pockets 209a of sponge bags 209. This allows the sponge bag counter rack system 207 to further provide weights associated with the stored used sponges 210 so that the system 207 may assist with detecting/estimating blood loss during and/or after a medical procedure to assist with transfusion decision-making and/or identifying or at least alerting users as to post-procedure patient risks, such as anemia which can eventually lead to adverse cerebrovascular outcomes (e.g., stroke, particularly in cardiac procedures) and can identify hemorrhaging concerns such as post-partum hemorrhaging in obstetrics which can lead to hemorrhagic shock and organ failure.

In the form illustrated, the system 207 may use the weighing scales 207g to perform a gravimetric analysis of the used sponges 210 in bags 209, however, in a preferred form, the system 207 will also utilize at least one additional technique for redundancy and to improve the assessment made relating to blood loss. In the form illustrated, the sponge bags 209 are provided in a translucent material so that a conventional physician assessment (or medical personnel assessment) can be made as one means of redundant checking. However, in a preferred form, system 207 will also utilize the camera 207f for capturing a picture of the used sponges 210 as they are passed by interface 207e and placed into their respective pockets 209a of sponge bags 209 as detected by an RFID/RF detection system similar to the one discussed above where the system 207 includes an active detector 207c either attached to (like FIG. 1) or integrated into tablet 207 and the sponges 210 include a passive sensor such as RFID/RF tag 210a. In this way, the system 207 may also use a photometric analysis (or assay analysis) and/or a computer vision algorithms and feature extraction analysis method like those discussed above to perform a redundant analysis (or series of redundant analyses) of EBL and/or Hb levels associated with the patient undergoing the medical procedure. In this way, the system 207 can utility numerous methods for detecting EBL and Hb levels in an effort to come to a more accurate assessment of true EBL and Hb levels and/or to flag or alert to discrepancies between the methods used for same.

In a preferred form, the system 207 will include memory (either onboard memory or remote memory either located on a remote device/at a remote location or cloud based memory) to store data related to each medical procedure so that this data may be compiled to identify common traits of successful procedures/outcomes and/or traits associated with unsuccessful procedures/outcomes in order to educate/ train medical personnel on such procedures and/or alert medical personnel in real-time as to issues that are being noticed that need to be addressed in order to ensure a successful medical procedure. This data may be compiled and built-on to continue to improve procedures and training and access to same may be provided either free of charge or under a paid subscription service in order to give access to all the data collected and information learned via same.

In the form shown in FIG. 2, the sponge counter rack system 207 communicates with a remote device, such as medical device reconciliation system 208 to relay data relating to the used sponges 210 and, in particular, data relating to the sponges 210 that have been stored on the rack 207 and those that are still missing, data relating to the estimated EBL and Hb levels using any one of the above explained techniques for measuring same. As with FIG. 1, the reconciliation system 208 will preferably include a cart 240 with one or more detachable wands 220, interface 230 and network interface 250 with optional onboard or remote memory 260. As mentioned above, the reconciliation system 208 may also include a smart wand 220 having a controller 226 and one or more of a proximity sensor 222 and/or a motion sensor, such as accelerometer 223. In some forms, the reconciliation system 208 will also include a scanner 270 that can be used to scan out and in items used in the medical procedure so that the system 208 alerts to any missing items before a procedure is closed-out. In a preferred form, the scanner 270 is removable from the system 208 (e.g., or cart 240) so that it can be used remotely to scan items that are not easy to pass by the scanner 270 in its normally stored position on cart 240.

In a preferred form, the sponge counter rack system 207 of FIG. 2 will include a notifier that alerts or notifies the user of data relating to sponges 210. In one form, the notifier may be one or more of a display, a light, a buzzer, a speaker, a haptic feedback device and/or a communication circuit capable of transmitting a communication advising of data relating to the sponges 210 (e.g., sponge presence or absence, the EBL and/or Hb determination, excess fluids/tissues detected with sponge beyond blood, etc.). In some forms, the notifier includes the communication circuit 207e and the communication circuit 207e is configured to communicate via at least one of wireless fidelity (Wi-Fi), Cellular, radio frequency (RF), infrared (IR), Bluetooth (BT), Bluetooth Low Energy (BLE), Zigbee and near field communication (NFC).

As mentioned above, the smart sponge counting rack system 107, 207 may include an external antenna for the communication module 107e, 207e to use to detect the presence of used sponges 110, 210 via their tags 110a, 210a as they are placed into pockets 109a, 209a of sponge bags 109, 209. For example, in FIG. 3, there is illustrated an example of the embodiment of FIG. 2 showing linear antenna 207h which may be positioned in or on the pole of IV pole 207d and used to detect sponges 210 as they are placed in pockets 209a. As mentioned above, in a preferred form, the system 207 is configured such that interface or communication module 207e includes a sponge detector 207c that is an active RF/RFID device which energizes a passive tag 210a on sponges 210 as they are brought within a read-range of the active sponge detector 207c.

Figure 4:
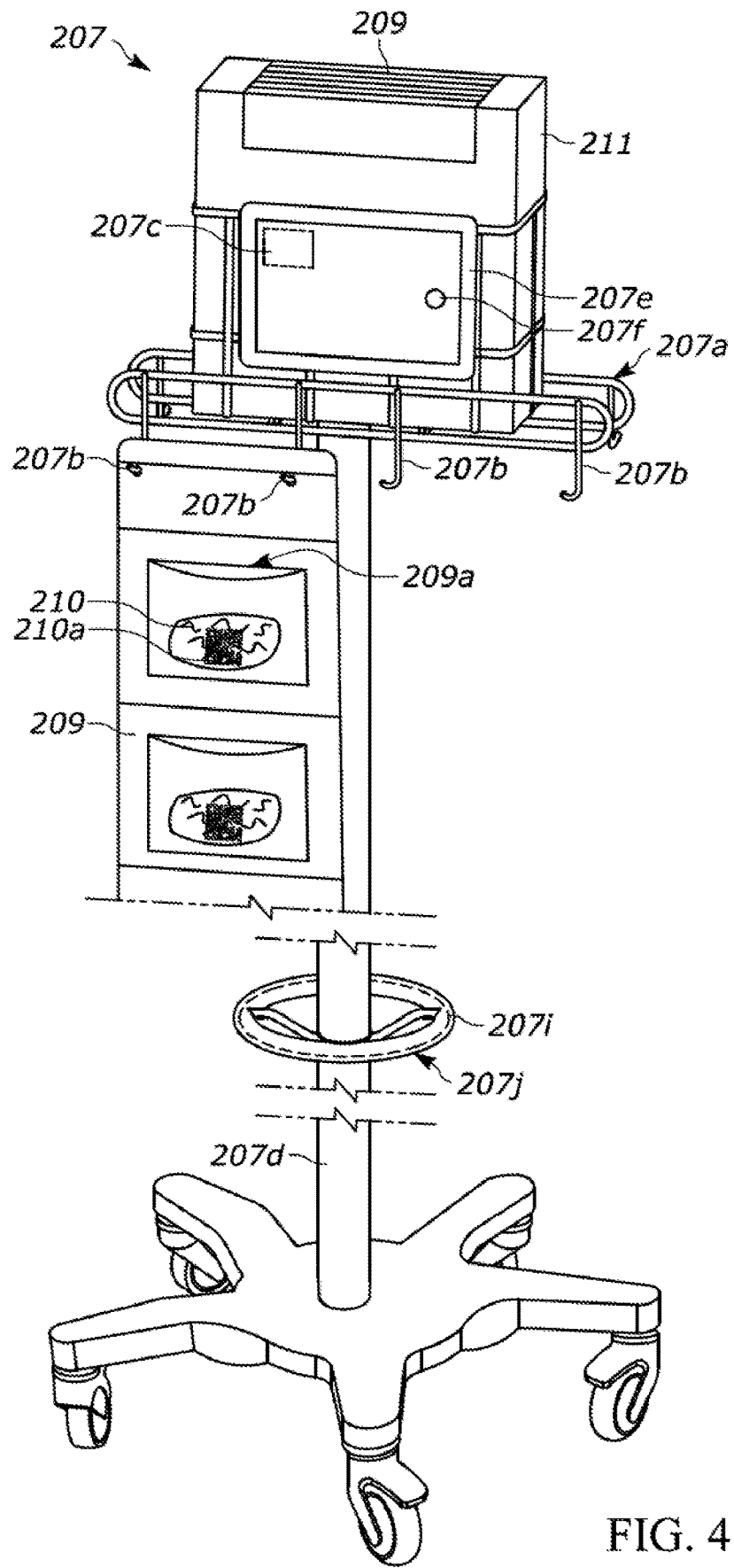
FIG. 4 is a partial perspective view of a medical device with an integrated radial antenna in or on a portion of the medical device or medical device accessory (e.g., such as a handle for an IV pole) for detecting the presence of a medical object within a predetermined read range in accordance with features of the invention.

In alternate embodiments, a radial antenna such as radial antenna 207i in FIG. 4 may be used as the external antenna for detector 207c. In the form shown, the radial antenna 207i may be connected to or embedded in a conventional IV pole accessory, such as wheel handle 207j. In this way, accessory attachments for a conventional IV pole 207d may be sold for use with either system 207 or 107 if desired. In the form illustrated, a common wheel handle 207j for an IV pole 207d is shown, however, in other forms, the accessory may be the antenna itself (e.g., 207h, 207i, etc.) which can be attached to the IV pole 207d where desired and connected to communication module 207e either physically or wirelessly. In some forms, a combination of linear and radial antenna 207h, 207i may be used if desired.

While the embodiments illustrated in FIGS. 1-4, all illustrate a sponge counter rack system 207 that is connected to a conventional IV pole 207d and support two separate sponge bags 209 on each side, it should be understood that alternate embodiments of system 207 may be provided that are wall-mounted and/or include one or more sponge bags 209 as illustrated in FIG. 5. In keeping with prior practice, items that are similar to those discussed above with respect to FIGS. 1-4 will utilize the same latter two-digit reference numerals, but use the prefix "5" to distinguish one embodiment from others. Thus, in the form illustrated in FIG. 5, the system 507 includes a body 507a having a plurality of supports 507b which are used to suspend at least three sponge bags 509 and defines a recess for retaining container 511 for dispensing bags 509. Unlike prior embodiments, however, the system 507 is wall-mounted (instead of IV pole mounted) and is capable of supporting three separate sponge bags 509 if desired. In still other forms, the system 507 may be configured to suspend or support any number of sponge bags desired and/or may include any of the other features discussed above with respect to other embodiments (e.g., weight scales, different sponge bag containers, different body configurations, etc.). In a preferred form, the body 507a will include mounts for mounting body 507a to a wall so that sponge bags 509 may be suspended from the wall and used to store used sponges 510 having tags 510a during a medical procedure. While the embodiment shown shows three bags 509 arranged in column format with each bag having a plurality of pockets 509a for receiving individual used sponges, it should be understood that the system 507 may be configured to support any number of sponge bags 509 and any number of pockets 509a within sponge bags 509.

In the form illustrated in FIGS. 1 and 2, the sponge counter rack system 207 and reconciliation (or reconciling) system 208 are illustrated as two separate systems/devices for use during a medical procedure. In the forms illustrated, the sponge counter rack systems 107, 207 each include a first communication module 107e, 207e, and a separate second communication module 150, 250 of sponge reconciling system 108, 208 to communicate with the first communicating module 107e, 207e. In the form illustrated, the first communication module 107e, 207e of smart sponge counter rack 107, 207 provides data to the second communication module 150, 250 of system 108, 208 so that the separate sponge reconciling system 108, 208 can provide real-time information relating to the smart-sponge counter rack system 107, 207.

It should be understood, however, that in alternate embodiments these systems 207 and 208 may be integrated into a single system if desired. For example, in FIGS. 6 and 7, there is illustrated an integrated sponge counter rack and reconciliation system. In keeping with prior practice, items that are similar to those discussed above will use the same latter two-digit reference numeral, but the prefix "6" to distinguish this embodiment from others. Thus, in FIG. 6 there is illustrated a surgical area/arena 600 having a patient 602 and a patient support surface, such as operating table 604, and the integrated sponge counter rack and reconciliation system 607. The integrated system 607 includes a body 607a having a plurality of supports 607b for supporting sponge bags 609 for use during a procedure and, in an optional form, a recess or cavity defined by body 607a for receiving a container 611 containing dispensable sponge bags 609 that medical personnel 606 may dispense and suspend from supports 609b as needed. In FIG. 6 the system is integrated into its own standalone cart type system, whereas in FIG. 7 the system is built off of a conventional IV pole platform with modular items being connected thereto as accessories so that the system can be customized as the user desires. For example, in FIG. 7 the sponge counter rack 607 is connected to the IV pole via connector 6071 which suspends the sponge counter rack 607 off to the side of the IV pole 607d and allows the sponge counter rack 607 to be adjusted in height along the IV pole as desired by the user 606. In a preferred form, the connector 6071 has a clamp on one end to connect the connector 6071 to the IV pole (again at varying heights thereon as desired by the user) and has a mount on an opposite end that the sponge counter rack equipment is connected to in order to suspend the sponge counter rack off to a side of (or spaced apart from) the IV pole. More details on IV poles and IV pole mounts for accessories can be found in Applicant's prior U.S. Patent Application Publication Nos. US20130037663A1 published Feb. 14, 2013 and entitled Intravenous Fluid Container Stand and Methods for Making Same and US20170151386A1 published Jun. 1, 2017 and entitled Intravenous Pole Base Having Tessellating Elements, and prior U.S. Design Nos. D636871 issued Apr. 26, 2011 and entitled IV Pole Accessory, D634004 issued Mar. 8, 2011 and entitled IV Pole Accessory, and D631152 issued Jan. 18, 2011 and entitled IV Pole Accessory, which are all incorporated herein by reference in their entirety.

In the embodiment shown, the sponge bags 609 have a plurality of pockets 609a, but not all pockets have used sponges disposed in same. This may either mean that more sponges 609 are yet outstanding, or it may mean that the procedure involved only required the use of five sponges 609. With respect to the former, it can be seen how the translucent pockets 609a make it possible for the personnel or user 606 to quickly assess if there are outstanding sponges 609. In a preferred form, the pockets 609a are actually transparent so that personnel can also perform a visual assessment of the patient's EBL and Hb levels to alert if any concerning conditions are present (e.g., like the physician assessment or eyeballing assessment discussed above).

Figure 3:
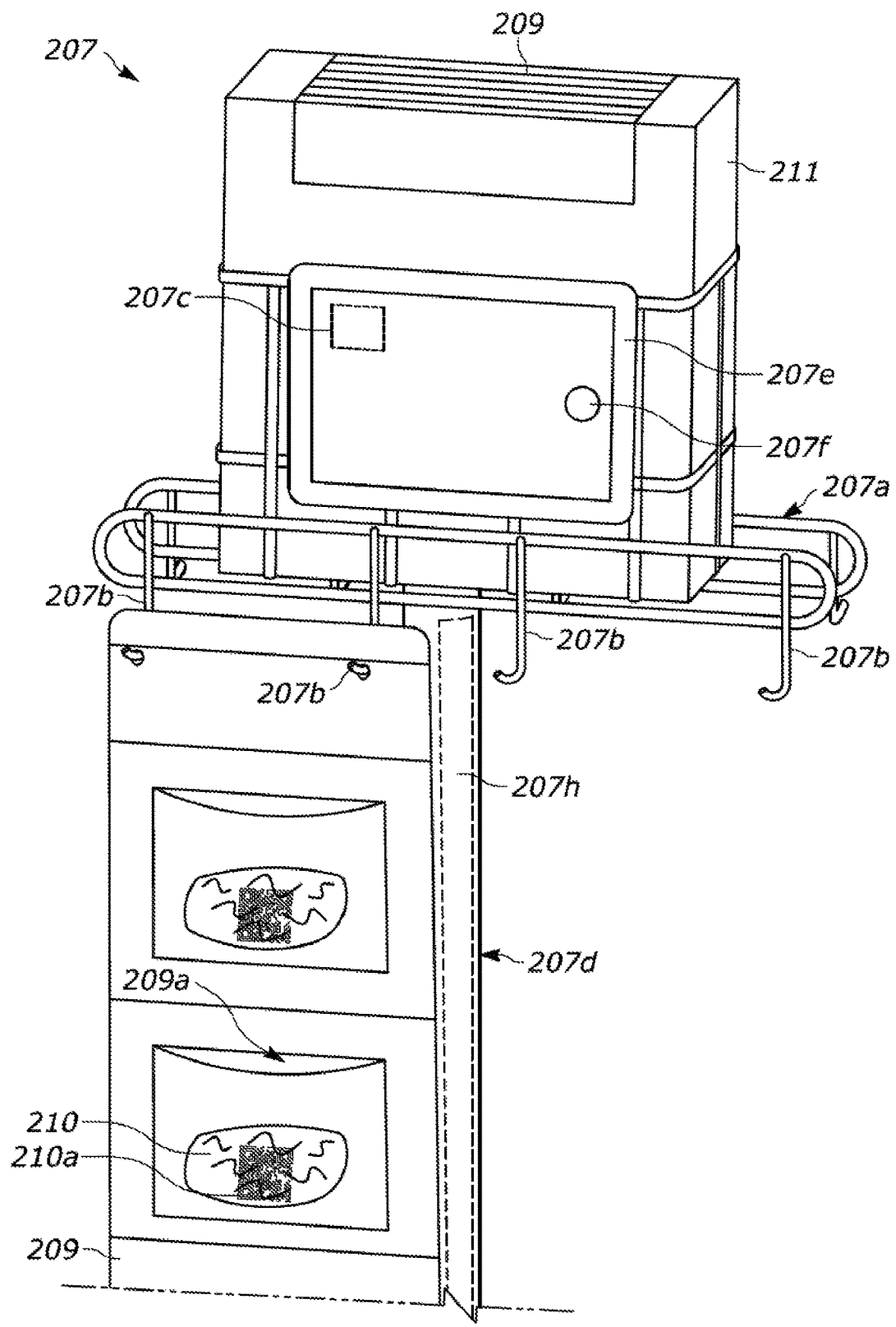
FIG. 3 is an enlarged perspective view of a portion of a medical device (e.g., an IV pole) with an integrated linear antenna in or on the medical device or medical device accessory for detecting the presence of a medical object within a predetermined read range in accordance with features of the invention.

Unlike the prior embodiments of FIGS. 2, 3 and 4, in this embodiment, the sponge detector 607c is separate and apart from the interface 607e. In the form shown, the sponge detector 607c is an active device that is contained in its own housing and energizes passive devices such as tags 610a on sponges 610 as they are brought within a read-range of the integrated system 607. In a preferred form, the detector 607c will be an active RF/RFID detector and the tags 610a will be passive RF/RFID tags.

Also, unlike prior embodiments, the system 607 includes two wands 620 that one or more users may use to scan the patient 602 or surrounding surgical area/arena 600 (including table 604). In FIG. 6 user 606 is shown using one of the wands 620 and the upper side of the wand 620 is shown (i.e., the side opposite the side having the proximity sensor 622 and speed sensor 623). In one form, the uppers side of the wand (or side facing the user 606 when in use) will include indicator 624 which may be at least one of a visual device, an audible device and/or a haptic feedback device, or any combination of these. In one form, the indicator 624 will be a visual device including at least one display. More particularly, in a preferred form, the display will comprise one or more lights, such as light emitting diodes (LEDs), or one multi-colored light, such as a multi-colored LED that can change from one color to another color to represent different states or conditions. In the form shown in FIGS. 6 and 7, the indicator 624 is a display comprising a first LED 624a and a second LED 624b. The first LED 624a is a green LED and the second LED 624b is a red LED. When the wand 620 is outside of the desired scanning range from the target area to be scanned, the second/red LED 624b is illuminated to indicate to the user 606 that the wand is not within the proper scanning region or range. When the wand 620 is within the desired scanning range, the first/green LED 624a is illuminated to signify that the wand is within the proper scanning range. In a preferred form, the proximity sensor 622 is located on a first side of the wand 620 intended to be held face down by user 606 (or facing the target area to be scanned) and the indicator 624 is located on a second or opposite side of the wand 620 intended to be visible to the user 606 as the proximity sensor 622 is held face down during scanning. In this way the user 606 can see the display 624 (e.g., LEDs 624a, 624b) while he or she is scanning the target area with the wand 620. In alternate forms, however, it should be understood that these items may be positioned on the same side of the wand 620 as each other (particularly in instances where the indicator 624 is not a visual indicator, but rather an audio device or haptic feedback device) or they may be faced on other sides of the wand that are not opposite one another such as adjacent sides, etc.

While two LEDs are shown (i.e., 624a, 624b), it should be understood that other forms of visual devices may be used. These alternate visual devices may be similar to LEDs, such as a multi-colored LED that can change from a first color (e.g., green) to a second color different than the first (e.g., red). Alternatively, a single light may be used (e.g., a green LED light solely to indicate when the wand is within read range, alternatively a red LED light solely to indicate when the wand is not within read range, etc.). In yet other alternate forms, different types of visual devices may be used entirely, such as a screen display (e.g., LED or LCD screen display, vacuum tube display, graphical user interfaces (GUIs) or touchscreens, needle-type analog meters, light bars, etc.). In addition, rather than just illuminating one light of color, the display 624 may illuminate multiple lights of the same or different colors to indicate proximity (e.g., illuminating a first light or first series of lights to indicate the wand 620 is not in proper scanning range and then a second or second series of lights to indicate the wand 620 is in proper scanning range). Multiple lights may also be used to indicate the proximity of the wand to the target area to be scanned and/or its strength of scanning at the range it is currently held at with respect to the target. For example, in some forms, the display 624 may illuminate with one light (e.g., one green LED) once the read range threshold has been reached, and continue to illuminate similar colored lights as the wand moves closer to the target scan area to indicate the wand is closer and that stronger scanning capability is possible at the closer range (e.g., illuminating a second green LED when the wand gets to an intermediate position between the read range threshold and the target scan area, and a third green LED when the wand gets to a very close proximity of the target scan area (closer than the intermediate position)). If more lights are desired, the range between the read range threshold and the target scan area can be broken up even further with lights representing each of those dissected areas. In still other forms, the light bar may illuminate a red light to indicate outside the read range and then others to indicate within the read range and signify the proximity to the target scan area.

As mentioned above, the indicator 624 may include an audio or audible device (this may be in addition to the display device or in lieu of the display device). Any conventional audible device may be used such as one or more of a speaker, buzzer, horn, etc., so that an audible alert can be provided when the wand 620 is within proper scanning range, when it is outside of proper scanning range, both (e.g., distinguishing the audible signal to distinguish whether the wand 620 is within proper scanning range or not), or simply when the read range threshold has been reached and that is it as discussed above with the visual display device. In a preferred form, the audible device indicator 624 will use a buzzer to make an audible alert or signal when the wand 620 is first brought within the read range of the target area (e.g., within twenty inches (20")) to alert the user 606 the wand is now within the appropriate scanning range so that the user 606 can start scanning and looking for retained objects. In other forms, the audible indicator 624 may be used to alert the user 606 if the wand leaves the proper scanning range, such as by issuing a sound signal from the buzzer once the wand leaves the read range.

In a preferred form, the wand 620 may further include a mute input the user 606 can use to mute the audible indicator 624 so as not to annoy the user with the sound when the user intentionally has to move the wand outside of a specified area. In such forms, it is desired to keep the muting to a minimal amount of time to ensure the user 606 is properly notified if the wand 620 again leaves the proper scan range or read range, but in some forms the system may be configured to allow for predetermined periods of muting (e.g., five seconds (5 s), 10 seconds (10 s), 30 seconds (30 s), etc.) or may even allow the user to turn off the audible alert entirely if desired. In some forms, this input may actually be an "interrupt" input that allows users to turn on/off the various types of scanning features discussed herein. For example, a user with administrator-level permission, may be able to interrupt the indicators and notifications of the system, including interrupting the normal workflow of the system, not just temporarily muting sound. This may be desirable in situations where training with the wand is being performed and, thus, the user does not want the data collected to be combined with the data that is collected during actual procedures so as not to distort the actual procedural data collected to-date. For example, in some forms, the mute feature or function will be an input the user simply actuates to cause the system to go quite for a predetermined period of time. In other forms, the mute feature or function (as will all functions discussed herein) may be controlled by a software setting so the user to can set whether or not he/she wants a muting feature and/or, if he/she does, how long the muting feature will last for in one or more different situations. Thus, the mute feature or function may be controlled by either a hard or soft button input (e.g., either by a hardware input that is physically operated (e.g., a hard button solution) or by a software setting (e.g., a soft button solution)), or both. In one form, the mute feature or function is enabled or disabled via software operating on controller 607e. In other forms, it is a physical input or button located on the controller 607e and/or on any one of the modular devices used in the system (e.g., wand 620, scanner 670, tablet 607e, etc.).

In alternate forms or in forms where the indicator 624 includes more than one form of indicator, the indicator 624 may include at least one haptic feedback device. In one form, the at least one haptic device is an actuator that vibrates when the wand 620 is either outside of the proper scanning range or within the proper scanning range. In a preferred form, the actuator is at least one of a vibratory motor or a linear resonant actuator that causes the wand to vibrate when the wand is outside of the desired scanning range or read range. Thus, as user 606 is using the wand 620, they will receive some form of haptic feedback, such as vibration, if they raise the wand 620 above the desired scanning range (e.g., above twenty inches (20")). In other forms, the haptic feedback may be used to signify when the read range threshold has been reached.

As mentioned above, in alternate forms, any combination of the above-mentioned indicators may be used as indicator 624. For example, in a preferred form, the wand 620 will be equipped with all three indicators (e.g., visual, audible and haptic) and the audible device will emit an audio signal or alert when the wand 620 is brought within the read range of the target area to be scanned (just at the read range threshold) and will illuminate the visual device, such as green LED 624a, to signify to the user 606 that the wand 620 is within the proper read range. Once the user removes the wand 620 from the proper read range, the red LED 624b will illuminate and the haptic feedback device will continue to vibrate the wand 620 until the user 606 returns the wand 620 back to within the proper wand read range or returns the wand 620 to a storage location. In this way, the user is provided multiple different indications as to whether the wand 620 is within the proper scanning range while the user 606 is passing the wand over the medical procedure area 600. In a preferred form, this redundancy is used in order to ensure the user knows when the wand is within the proper read range and when he/she is outside the proper read range to ensure scanning with the wand is done only within the proper read range. In still other forms, one of the indicators will be used to indicate when the wand 620 is outside the proper read range (e.g., red LED 624b), another indicator will be used to indicate when it has crossed the read range threshold (e.g., audible sound such as a beep) and a third is used to indicate if the motion sensor 623 detects that the wand is being moved at an improper speed or with an improper orientation (e.g., haptic feedback to indicate this). Any combination of the indicators can be used to achieve these same distinctive notices or alerts.

Figure 6:
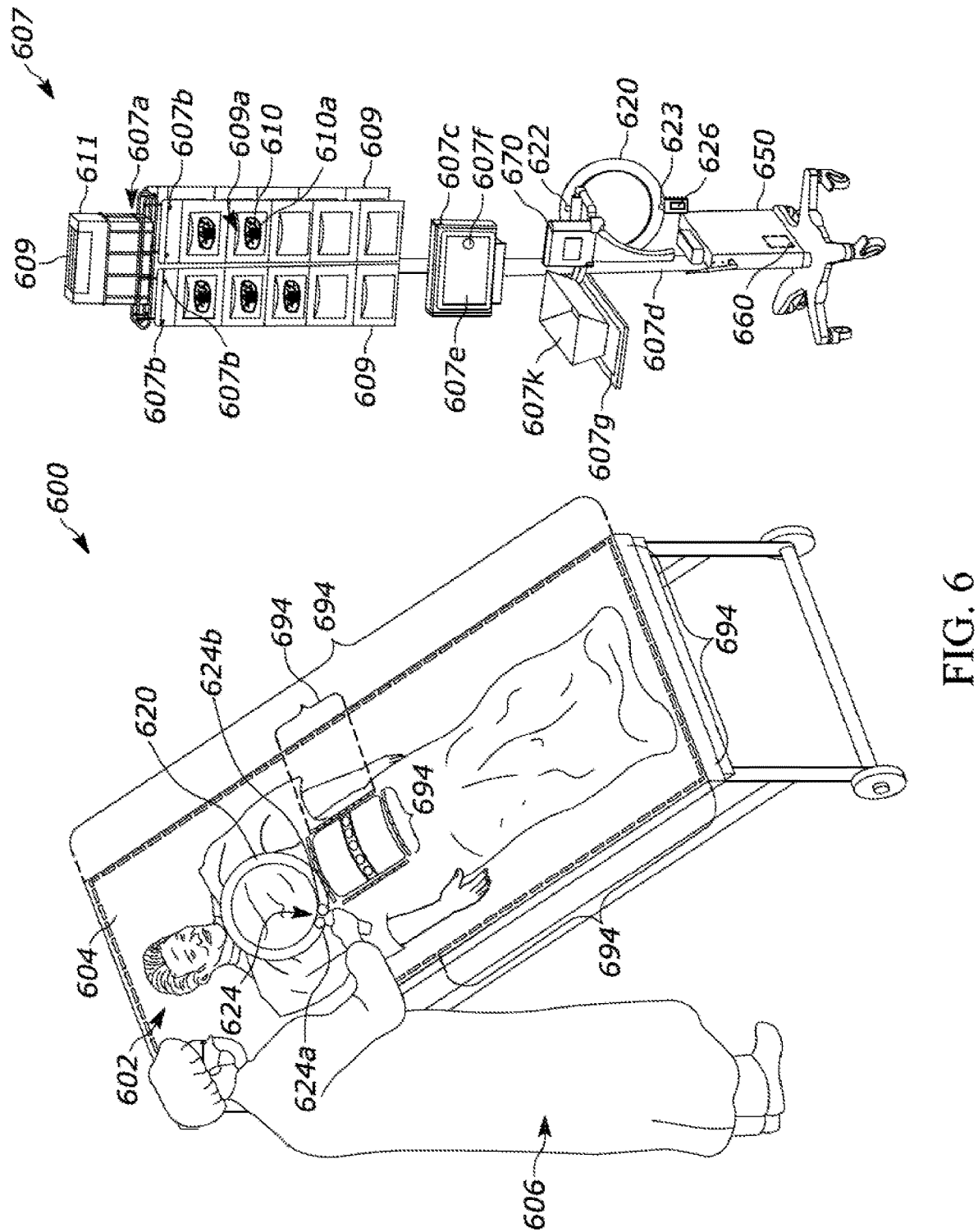
FIG. 6 is a perspective view of a medical procedural area/arena illustrating use of an integrated medical object counting system and medical object reconciliation system, with one or more EBL and hB detection capabilities in accordance with features of the invention.
Figure 7:
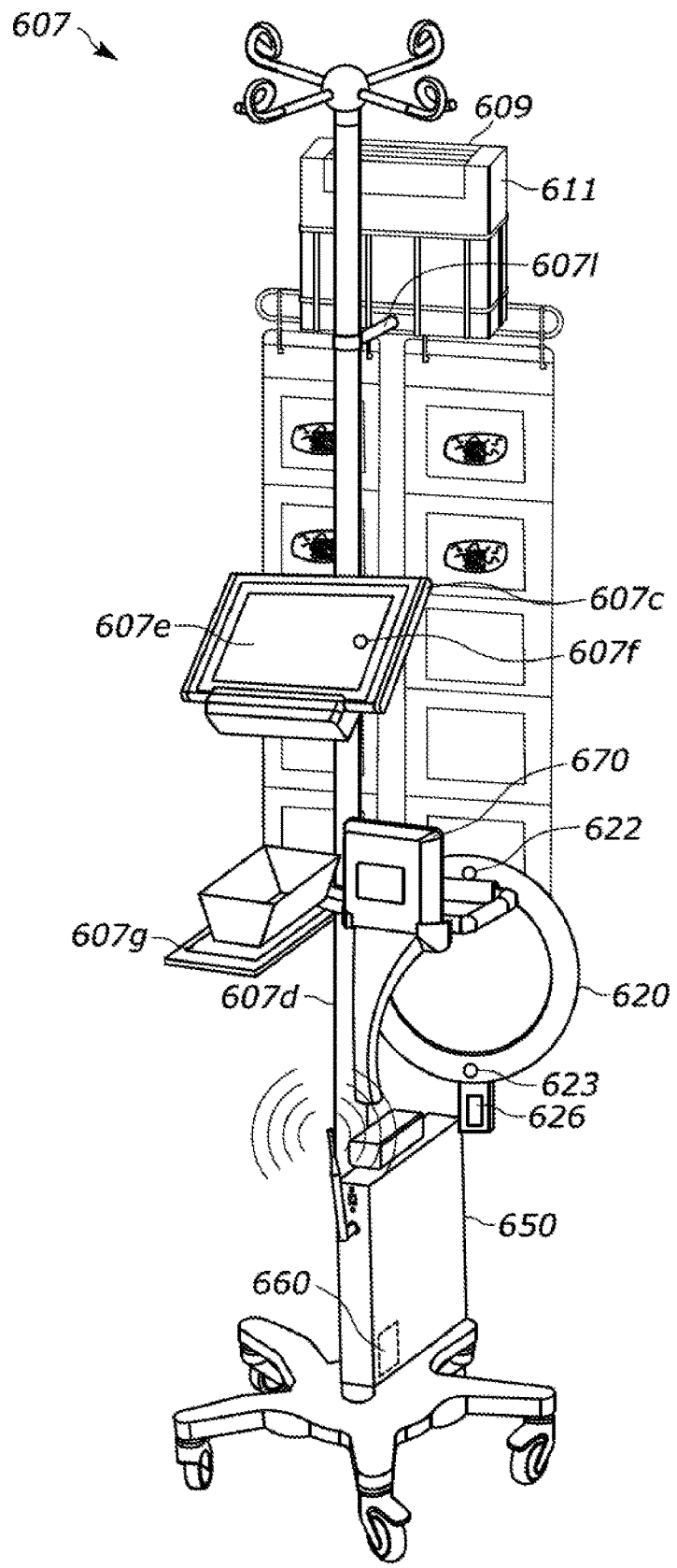
FIG. 7 is a perspective view of an alternate integrated medical object counting system and medical object reconciliation system in accordance with features of the invention illustrating a system similar to FIG. 6 but having the sponge counter rack as an accessory suspended from another piece of equipment such as a conventional IV pole.

In the form shown in FIGS. 6 and 7, the wand 620 further includes a controller, such as integrated circuit or processor 626, which is electrically connected to the proximity sensor 622 and indicator 624 (either directly or indirectly) and controls operation of the indicator 624 based on the input provided from proximity sensor 622. In a preferred form, the controller 626 will be positioned on the same printed circuit board containing the wand antenna and the indicators present for that particular wand (e.g., visual indicator device, audible indicator device and/or haptic indicator device). In this way, the wand 620 could be sold as its own stand-alone product if desired. In alternate forms, however, the wand 620 may be sold as a module system that can include numerous other modules or components or be provided at different product tiers (e.g., good/entry level with less options, better/mid-level with slightly more options, best/high-level with all options, etc.). For example, the form shown in FIG. 5 may be considered a basic entry level product as it has no sponge detector, while the version shown in FIG. 1 is marketed as a slightly better level product because of the presence of the sponge detector and communication module, and the embodiment of FIGS. 3 and 4 are slightly better yet in that they include an interactive GUI such as a tablet, and with the embodiment of FIG. 2 being considered still better in that it includes the interactive GUI as well as scales to weigh the sponges, etc.

In the form shown in FIGS. 6 and 7, the integrated system 607 combines the interfaces for the sponge counter rack system and the reconciliation system into one controller or interface, such as touch screen display 607e. In a preferred form the wand 620 will be wireless and the touch screen 607e will be a wireless tablet that can be mounted to a mobile cart 607d for mobility and storage. In this way, the user 606 may carry the interface 607e with them if desired as they use the wand 620 (e.g., such as in situations where the proximity information or display 624 is provided on the interface 607e only and not on the wand 620 itself). By separating the sponge detector 607c from the interface 607e, this allows the integrated system 607 to continue to detect sponges 609 as they are placed in pockets 609a via detector 607c even though the control interface 607e may be removed from cart 607d.

In some forms, the integrated system 607 will include its own network connection 650 in order to ensure a highly efficient and private or dedicated local area network that the wireless wand 620 and wireless tablet interface 607e communicate over without having to worry about connecting to another network (such as a public network or network used generally among the medical facility). This wireless connection 650 generates an autonomous dedicated wireless network (e.g., Wi-Fi network) for the system that the system components may use to ensure efficient wireless communication between all components (e.g., sufficient bandwidth, sufficient connection signal, sufficient speed, etc.). If desired, the dedicated network could be opened up to other wireless components used in the procedural arena 600, however, in a preferred form this would require the entry of a password in order to keep the wireless connection 650 secured and protected from unwanted or unauthorized devices from being able to join the network.

Another component that may be included with the integrated system 607 is a memory 660. In the form illustrated in FIGS. 6 and 7, the memory 660 is shown for exemplary purposes as contained within the same structure as wireless network 650, however, it should be understood that memory 660 could be a local memory located elsewhere on the system 607, such as in interface device 607e or elsewhere on the cart 607d such as in its own housing attached to pole 607d, or alternatively it could be located remotely from the integrated system 607 depicted via a network connected memory (not shown). For example, the memory 660 may be a cloud-based memory located at a cloud storage facility remote from the remainder of the system 607 and accessible via a wide area network, such as the Internet. In some forms, the system 607 will communicate to a remote database via a standard communication protocol. For example, in one form, the system 607 will communicate with the remote database via a cellular protocol or signal using either a cellular transmitter included with system 607 or via a third-party device, such as a user's mobile phone, via software (e.g., an App) downloaded on or to the third-party device.

Another additional component that may be included with the integrated system 607 is a scanner 670 for scanning instruments or their packaging to check them out prior to the procedure and/or check them in or reconcile them by confirming they are not still unaccounted for once the procedure is done to alert the users that an item is missing if in fact that is the case. In a preferred form, the scanner 670 will be able to read machine detectable or readable markers, such as bar codes, RFID sensors, alpha sequential markings, numeric sequential markings, alpha-numeric sequential markings, or just comprise a machine detectable image or shape. For example, in some forms, the instrument marker includes a bar code identifying the instrument and/or containing information about the instrument, such as a UPC, EAN, GTIN or other trade identification for identifying an item. For example, the scanner 670 may scan linear, two- or three-dimensional (2D, 3D) hydrophobic markings and be used by the user to scan in the items that will be used for the procedure so that those same items have to be rescanned in later once used in order to do an audit or reconciliation of the items used. The RF/RFID tags 610a discussed above may also include such machine detectable identifiers so that scanner 670 is also used to check out sponges 610 and then sponge detector 607c is used to check them in once they are stored in respective pockets 609a of the sponge bag 609 or at least brought within the read range of sponge detector 607c. If an item is not scanned back in, then the user will take the wand 620 and search for the missing item. In the form shown, the scanner 670 includes a head with an elongated handle extended therefrom. The scanner 670 includes a scanner (such as an optical laser reader) on one side and has its own display on the other opposite side to indicate what item was scanned in order to allow the user 606 to perform a redundant check confirming that the item being checked out is in fact the desired item to check out during the procedure. In one form, the scanner 670 can stay mounted on the cart 607d and simply have the items held up in front of the optical side of the scanner 670 to register them with the scanner 670. While in other forms, the scanner 670 can be removed from the cart 607d and handheld to hold the optical side of the scanner face down over the item to be scanned to scan same and indicate on the display located on the side of the scanner 670 facing upward opposite the optical scanner side what item has been scanned.

Yet another item that may be included with integrated system 607 is a receptacle, such as basin 607k, which used sponges may be placed in so that the system may photograph the sponge 610 via camera 607f so that an assessment can be made on same to help determine the patient's EBL and Hb levels and alert if there are any concerns regarding same or conditions that may result regarding same. In a preferred form, the basin 607k will position the used sponge so that the camera 607f can take a clear image of the used sponge 610 and will also bring the sponge within the proper read range of sponge detector 607c so that the sponge can also be detected at the same time to automatically pair the photo with the actual sponge 610 it relates to and to store this data electronically without the user needing to do anything further. In some forms, the basin 607k will be translucent and preferably even transparent so as not to interfere with the camera's ability to get a clear picture of used sponge 610. In some forms, the integrated system 607 will also include a scale 607g positioned under the receptacle or basin 607k in order to automatically weigh the sponge 610 at the same time as it is being photographed by camera 607f and checked in by detector 607c. In this way, all of this data may automatically be logged for the exact sponge being checked in and stored together without the need for the user to do any further cataloging or pairing of such data. In some forms, the pockets 609a of sponge bag 609 will be sequentially numbered so that the user knows what order to place the sponges in so that the exact pocket location of the sponge can also be electronically stored automatically should the need arise later on to go inspect or perform further analysis of the exact sponge in question. Similarly, the sponge bags 609 may be sequentially marked so that the user knows which bag to fill first and which to move to next, and so on, so that the exact sponge location can be catalogued electronically and the exact sponge can be located later on if necessary. In the form shown in FIGS. 6 and 7, the scale 607*g* rests atop a flat surface, such as a shelf or table top surface, and the receptacle or basin 607*k* rests upon the scale 607*g*. The receptacle or basin 607*k* can be rinsed between sponges so that fluid or other substances (e.g., tissues, gauze, etc.) from one sponge do not impact the data recorded for later sponges. However, in preferred forms, this will not need to be done as the system will simply calibrate the assessment of new sponges added to the basin 607*k* based on the basin's state prior to the new sponge being added so that fluid or other substance does not get double counted in the EBL and/or Hb assessment by the system.

In this way, the integrated system 607 not only allows for a visual assessment of the used sponges (e.g., physician assessment or eyeball test) and a gravimetric assessment of the used sponges (e.g., by weighing the sponges and making a calculation as to EBL and Hb), but also allows for a photometric analysis (or assay analysis) and/or a computer vision algorithms and feature extraction analysis method like those discussed above to perform a redundant analysis (or series of redundant analyses) of EBL and/or Hb levels associated with the patient undergoing the medical procedure so that conditions can more accurately be assessed particularly regarding EBL and Hb levels in determining need for transfusions and/or risks for anemic conditions that may lead to adverse cerebrovascular events (e.g., stroke) and/or hemorrhaging concerns (e.g., such as post-partum hemorrhaging in obstetrics) which can lead to hemorrhagic shock and organ failure. Thus, system 607 includes an EBL and/or Hb detector for monitoring EBL and/or Hb levels and/or dangerous conditions associated with same. In one form, the EBL and/or Hb level detector includes at least one of a visual assessment tool, a gravimetric tool, a photometric analysis tool, and/or a computer vision algorithmic and feature extraction tool. In other forms it may include any combination of these tools. For example, in one form an integrated EBL and Hb level detector is provided comprising a computer vision algorithmic and feature extraction tool including a camera for capturing images of used sponges and a controller for analyzing the captured images and extracting features from the captured images to obtain a more accurate EBL and/or Hb level associated with the patient. In still other forms, the system 607 may further include a notifier for providing a user with an EBL and/or Hb level associated with the patient. The notifier may include an alarm for notifying the user when a dangerous EBL and/or Hb level has been detected to assist in preventing complications for the patient. In still other forms, the integrated EBL and Hb level detector includes a gravimetric tool including a scale for measuring the weight of used sponges and includes a controller for calculating the EBL and Hb level by reducing the measured weight of the used sponges by a predetermined dry weight of unused sponges and any container they may be in such as receptacle 607*k* to determine the EBL and/or Hb level.

In addition to the above, integrated system 607 may also be used with markers, such as zone markers 694, which can be placed around the surgical area to help identify where missing items are located by wand 620 to aid in the retrieval of same and to provide valuable insight post procedure for training purposes and the like. In the form shown in FIG. 6, the zone markers 694 are passive devices that are energized by the wand 620 as it passes over same to indicate to system 607 where the wand is at the current moment in relation to the target area for scanning. In a preferred form, the zone markers will be RF/RFID tags like those used on sponges 610, however, in alternate forms they may consist of any other machine detectable configurations such as 2D or 3D bar codes, etc. In FIG. 6, the boarder of the surgical table 604 is lined with a first set of zone markers 694 that will indicate to the system 607 once scanned by wand 620 that the wand has reached the boarder of the operating table 604. A second set of zone markers 694 are then located around the surgical site of the patient's abdomen in this exemplary image and will indicate to system 607 when scanned by wand 620 that the wand 620 is now at the surgical site. This can obviously help pinpoint the system user as to where any missing items are located once the wand has detected same. For example, once a missing item is detected by wand 620, the wand or remainder of system 607 may display on a display what region of the surgical arena 600 the missing item was detected by the wand 620 so that the user can focus their efforts there. In some forms, the system 607 will be configured with a speaker (e.g., located on the wand 620, on the interface 607*e*, elsewhere on stand 607*d*, etc.) that audibly will announce the missing item and the location the wand 620 has detected same (e.g., an audible announcement of "Sponge 3, surgical site" or "gauze 2, foot region of operating table", etc.). In still other forms, the system 607 will simply make an audible noise (e.g., beep) or provide a visual indicator or haptic feedback when the wand 620 is located over the missing item.

In still other forms, the integrated system 607 may further be integrated with larger scale object retention systems such as those that are camera based that track movement of all surgical items throughout a procedure. In such instances, the integrated system 607 (or even the earlier separate systems 607, 608) may be configured to communicate and work with the larger scale object retention systems as desired. For example, in FIG. 8 the integrated system 607 is shown integrated into a larger scale object retention system. In keeping with prior practice items that are similar to those discussed above will use the same later two-digit reference numerals but include the prefix "8" to distinguish this embodiment from others. Thus, in FIG. 8, the interface of the integrated sponge counter rack and reconciliation system (e.g., 607*e*) is integrated into a larger scale object retention system 803 and illustrated by reference numeral 807*e*. A large-scale object retention system is disclosed in U.S. Pat. No. 10,154,885B1, issued Dec. 18, 2018 and entitled Systems, Apparatus and Methods for Continuously Tracking Medical Items Throughout A Procedure, which is incorporated herein by reference in its entirety. The controller or interface 807*e* is in electronic communication with a surgical area camera 890 and one or more wands 820. The surgical area camera 890 may have onboard memory 892, but in alternate forms this memory may be located elsewhere in the system 803 or remotely (e.g., cloud-based, at a remote central processing location, etc.). Alternatively, the camera 890 may have its own controller (e.g., located alternatively at 892) or interface 807*e* may control the operation of camera 890. In a preferred form, the camera will interface with system interface 807*e* similar to how the scanner 870 and wand 820 interface with system interface 807*e*. A variety of different types of cameras may be employed for camera 890, however, in a preferred form, only one camera 890 will be required for monitoring the desired procedural area, rather than requiring two or more cameras for monitoring specific portions of the procedural area (e.g., one camera for the prep table, another camera for the patient area, another camera for the waste receptacle(s), etc.).

The camera 890 will be connected to the system or apparatus via either direct connection via cable or wireless connection (e.g., RF transceiver setup, Wi-Fi, NFC, Bluetooth/BLE, etc.) or via a network interface which may also be wired (e.g., Ethernet, USB, etc.) or wireless (RF, Wi-Fi, NFC, Bluetooth/BLE, etc.). In a preferred form, the camera 890 will interface with controller 807e via the dedicated Wi-Fi network interface discussed above. The camera 890 may be connected in the procedural area in numerous different ways (e.g., connected to the ceiling, light fixtures, other existing medical equipment carts or towers, a prep table, etc.), however, in a preferred form, the camera may be mounted to the mobile cart containing the sponge counter rack and/or the reconciliation system and extended high above same via a boom or support beam extending from the cart so that it is brought into the procedural area by the medical personnel and not left there permanently.

Figure 8:
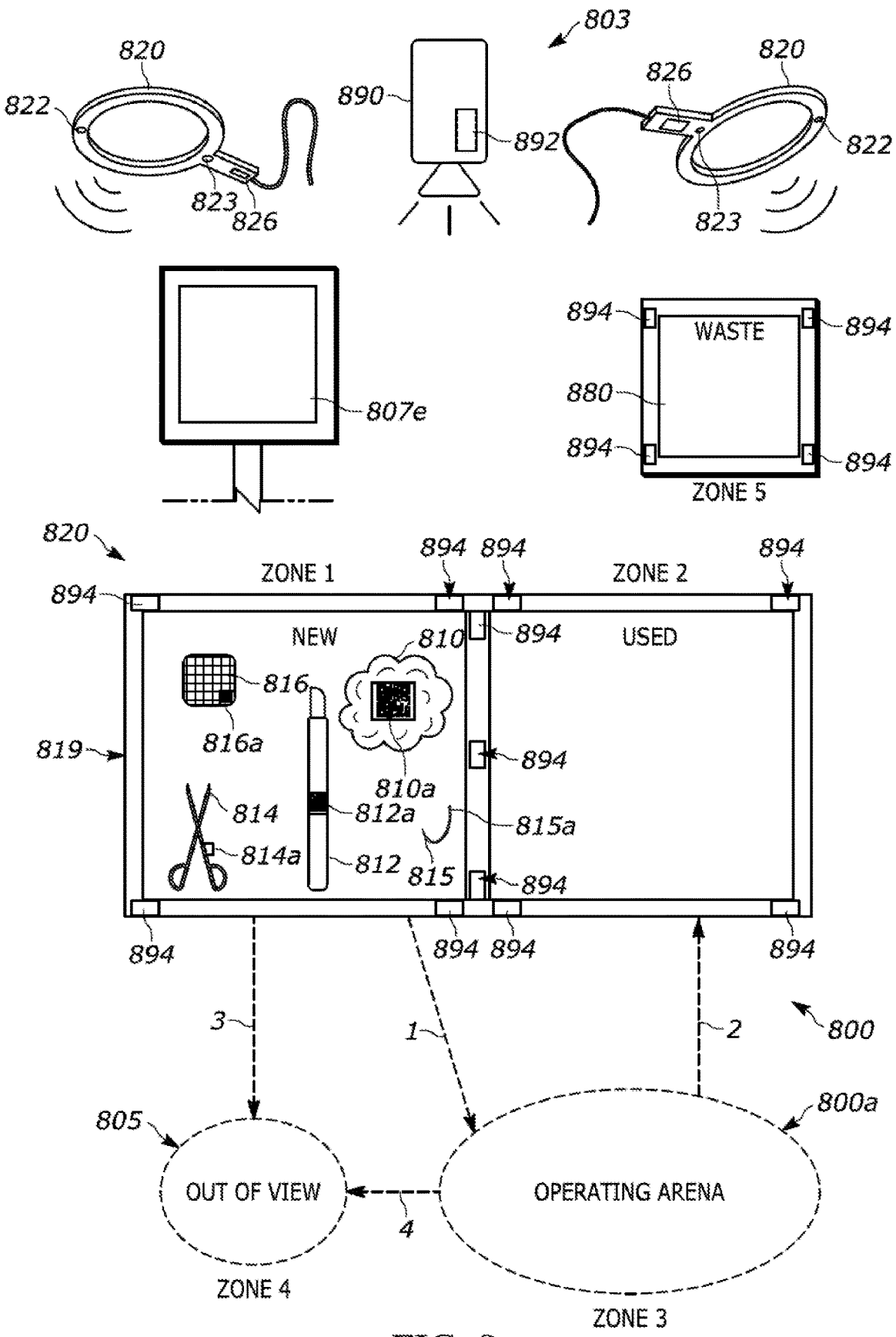
FIG. 8 is a perspective view of medical procedural area/arena illustrating use of an alternate medical object retention system having a camera for tracking medical objects throughout a procedure and a medical object counting system and medical object reconciliation system in accordance with features of the invention.

In the form shown and preferably, the wands 820 will include their own controllers 826, proximity sensors 822 and speed or orientation sensors 823, like the embodiments discussed above. Additional indicators such as visual, audible and/or haptic may also be used if desired and as discussed above. In a preferred form, all medical items that are to be used during the procedure will be marked with a machine detectable marker or tag that the camera 890 can detect. In FIG. 8, sponge 810 is marked with marker or tag 810a, scalpel 812 is marked with marker or tag 812a, forceps or scissors 814 is marked with marker or tag 814a, needle 815 is marked with marker or tag 815a, and gauze 816 is marked with marker or tag 816a. In the form shown, the marker or tags, are hydrophobic 3D tags, but these may also include passive or active sensors, such as RF or RFID tags.

The surgical area/arena 800 is marked with zone markers 894 to delineate a first zone or Zone 1 comprising a prep table, a second zone or Zone 2 comprising a used item or discard table, additional markers to identify a third zone or Zone 3 comprising the operating area/arena 800a, and a fifth zone comprising at least one waste receptacle 880. By default, the system 800 creates a fourth zone Zone 4 that is considered out of the view of the camera 890. Thus, as items (e.g., 810, 812, 814, 815, 816, etc.) are moved from the prep table of Zone 1 to the operating area of Zone 3 (see arrow 1 in FIG. 8), the camera 890 tracks this movement and provides updates on the status of each item on interface 807e. As the items are moved from the operating area of Zone 3 back to the used item or discard table of Zone 2 (see arrow 2 in FIG. 8) the camera 890 again tracks this movement and displays real-time data regarding the items on interface 807e. Similarly, if items are moved to the waste receptacle 880 of Zone 5, the camera 890 tracks this movement and provides real-time data regarding the discarded item on control interface 807e. If an item is lost by camera 890 during the procedure the system 803 notifies the user(s) that the item has gone out of view or to default Zone 4 and provides the user(s) with the last known data relating to the missing item (e.g., trajectory or direction of travel, speed, orientation data, etc.). In some forms, the system 803 will further provide a playback video showing the item and where it was right before it when missing or out of view. Once found, the system 803 will update the data relating to the missing item on interface 807e so that the users have real-time data of where all objects are during and after the procedure. The wands 820 of system 803 may also be used to help locate the missing items in the manner discussed above with respect to prior embodiments if the camera data alone is not sufficient to locate same.

In the form shown in FIG. 8, the interface of the larger scale object retention system 803 is integrated with or into the interface 807e of the integrated sponge counter rack and reconciliation system shown in FIGS. 6 and 7. However, in alternate embodiments, it should be understood that the controllers or interfaces of the systems do not need to be integrated in this way. For example, in some forms, the larger scale object retention system 803 may have its own interface and simply communicate back and forth with the interface (e.g., 607e) of the integrated sponge counter rack and reconciliation system (e.g., 607). In such a form, for example, the smart sponge counter rack system 607 will include a first communication module 607e and the separate object retention detection system 803 will include a second communication module (like interface 130, 230, etc.) and the first and second communication modules will communicate with one another in order to alert a user as to a retained object incident via either one of the user interfaces (or both) prior to allowing close out of the medical procedure.

In yet other forms, the sponge counter rack system and reconciliation systems may be their own standalone systems (e.g., 107, 108 or 207, 208, etc.) with their own interfaces (e.g., 130, 107e or 230, 207e, etc.) and the larger scale object retention system 803 may have its own interface or controller that simply communicates with these other interfaces or controllers. As mentioned above, these systems may utilize a dedicated network created by one of the systems that the other systems simply connect to, or they may alternatively use a broader network that exists at the medical procedure site such as a Wi-Fi network, etc. In still other forms, the devices may communicate with one another using other communication standards such as Bluetooth, NFC, or any of the other examples provided above. In some forms, the system will include the use of repeaters or similar such devices that can be used in the system to extend the read range of the equipment and activate tags that are located further away from the main RF or RFID reader. For example, the system may include one or more repeaters to place elsewhere in the procedural arena remote from the sponge counter rack or reconciliation system (or integrated version of same) so that sponges and other medical objects can be more accurately tracked throughout the procedure. In one form, a repeater accessory is place proximate the operating arena so that medical objects can be picked-up by the RF/RFID reader there effectively extending the read range of the RF/RFID reader located on the sponge rack and/or reconciliation system (or integrated version of same) so more accurately track the medical objects used during the procedure.

Thus, it should be understood that numerous different concepts and embodiments are disclosed herein including without limitation: smart sponges that can be detected by a sponge detection system; smart sponge counter racks that automatically detect the presence of used sponges disposed in pockets of a sponge bag suspended from the sponge counter rack and/or include EBL and/or Hb detectors; smart sponge counter racks that communicate with reconciliation systems and/or larger scale object retention systems; integrated sponge counter rack and reconciliation systems; integrated sponge counter rack, reconciliation and larger scale object retention systems; sponge counter racks, reconciliation systems and larger scale object retention systems that communicate with one another and work together to locate missing items and prevent object retention issues from occurring; and IV poles and IV pole accessories that help the above items perform their tasks.

Figure 9:
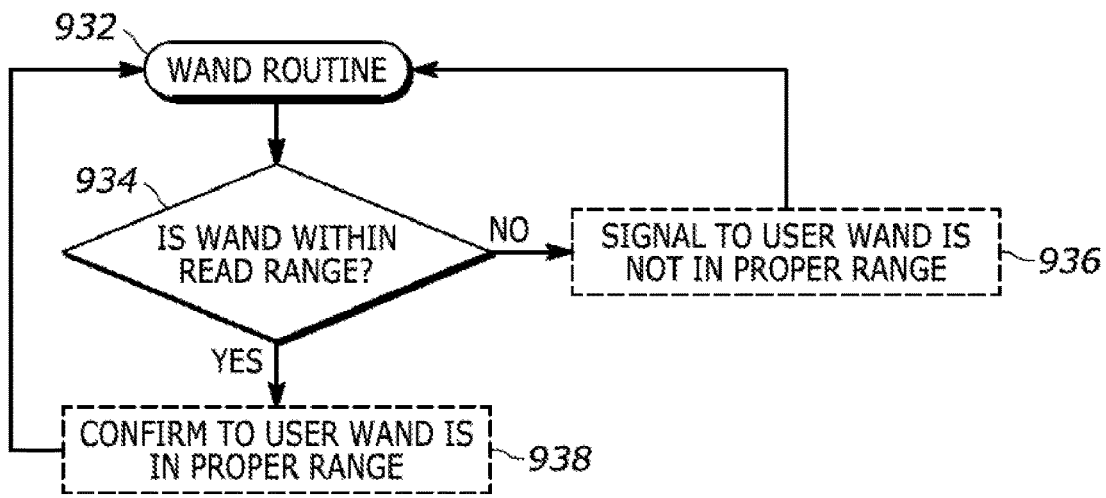
FIG. 9 is a flow chart illustrating an exemplary software routine operated by the medical object reconciliation systems discussed above.

A flow chart exemplifying a wand routine is illustrated in FIG. 9 and may be used with any of the embodiments discussed above. The wand routine is initiated in step 932, and a determination is made in step 934 if the wand (e.g., 120, 220, 620, etc.) is within read range or proper scanning range. It should be understood that the system can be setup in many different optional ways as discussed above. For example, in one form the system may be setup to only alert the user when the wand is not within proper read range (e.g., visual indicator, audible indicator, haptic indicator, combination and one or more of these, etc.) meaning the routine would jump to step 936. Alternatively, it can be setup to only alert the user when the wand is within proper read range (e.g., visual indicator, audible indicator, haptic indicator, combination and one or more of these, etc.) meaning the routine would jump to step 938. In a preferred form, however, the system will be setup to provide the user with feedback telling the user if the wand is outside of proper read range (step 936) and if the wand is within proper read range (step 938) so that the user can definitively tell at any given moment whether the wand is inside of or outside of proper read range. For example, the system will make an audible alert when the wand enters the read range threshold and illuminate a visual indicator (e.g., a steady light of a certain color, a flashing light of a certain color, etc.) to indicate same for as long as the wand remains in the read range. Once the wand leaves the read range, the wand will provide a haptic feedback via a haptic feedback device and illuminate a visual indicator (e.g., a steady light of a certain color, a flashing light of a certain color, etc.) indicating that the wand is no longer within proper read range for the entire time the wand is out of range until the wand is returned back to its mobile stand. In other forms, these notices or alerts may only be provided for a period of time (e.g., 5 seconds, 10 seconds, 30 seconds, 1 minute, etc.). For example, in one alternate form, the system will perform as discussed above with respect to the preferred form, however, the haptic feedback indicating the wand is not within proper read range will only last for 30 seconds and an audible sound will be made when the wand leaves proper read range to further alert the user of same. In other forms, the audible beep may be a continuous sound signal while the wand is outside of read range and/or it may be an audible signal that lasts for a predetermined period of time (e.g., see time examples above) In some forms, the user will be able to configure these options for the wand so that he/she can set it up as they would like it.

Figure 10:
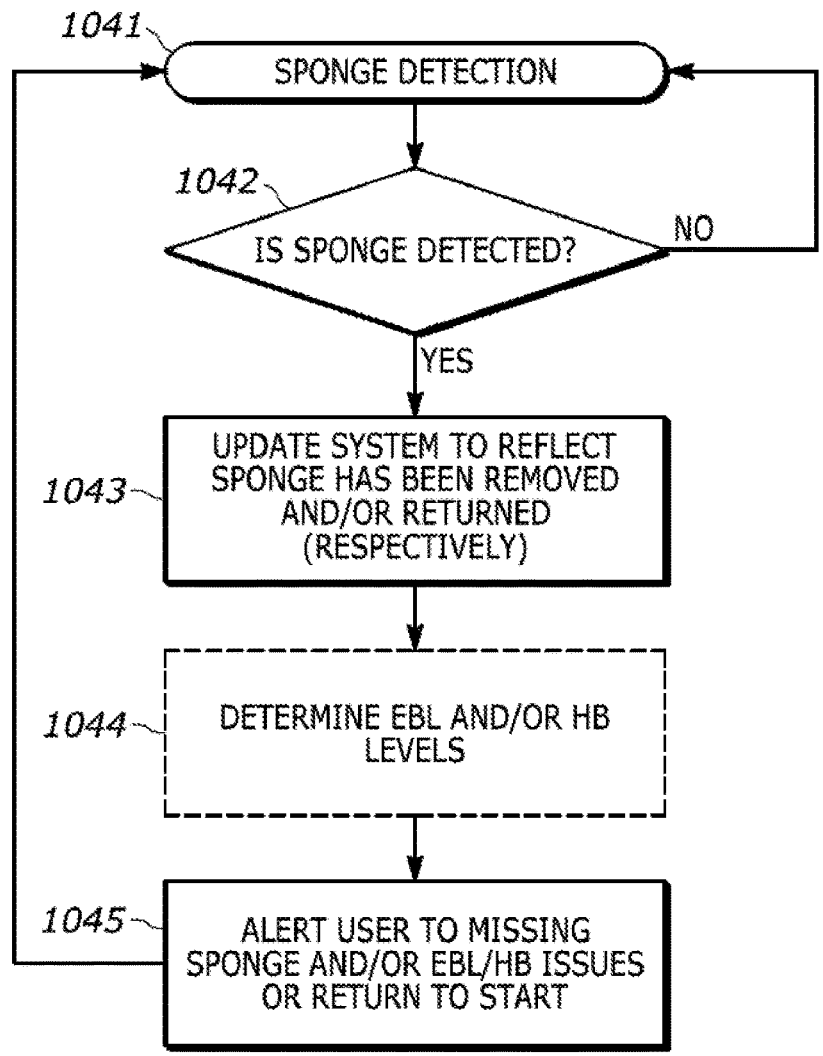
FIG. 10 is a flow chart illustrating an exemplary software routine operated by the medical object counting systems discussed above.

An alternate flow chart is illustrated in FIG. 10 that exemplifies a sponge detection routine that any of the systems discussed herein may follow (e.g., the sponge counter rack system 107 or 207, integrated system 607, etc.). The sponge detection routine starts at step 1041, and then a decision step is reached in step 1042 asking if a sponge is detected by the sponge detector (e.g., 107c, 207c, 607c, etc.). If not, the routine goes back to the start at 1041. If so, the system updates its records in step 1043 to reflect that a used sponge has been returned. Technically the system could be used to checkout sponges and check them back in so step 1043 references updating the records to reflect a sponge has been removed and/or returned, however, in a preferred form, the sponge detector will be used with the sponge counter rack and only care about whether a used sponge has been detected as being placed in one of the pockets of the sponge bag. In some forms, the process would simply return to start at step 1041 at that point or alert the user if a sponge is missing and the user is trying to close-out the procedure. However, in other forms, the process will then perform an analysis on the sponges to determine EBL and/or Hb levels in optional step 1044 and will alert the user in step 1045 if the While detailed systems and apparatus have been discussed thus far, it should be understood that broader claims can be made to a smart sponge counter rack comprising a sponge bag support for supporting a sponge bag containing a plurality of pockets, a sponge detector for detecting sponges that are brought within a read range of the sponge detector, a controller for operating the smart sponge counter rack and non-transitory computer readable memory storing a set of instructions executable by the controller (or control circuit) configured to indicate when a sponge has been brought within the read range of the sponge detector and to indicate the used sponge has been stored on the smart sponge counter rack.

In alternate embodiments, the set of instructions stored on the non-transitory computer readable memory will further indicate which sponge has been detected within the read range and what pocket the sponge has been stored in.

In still other embodiments, the smart sponge counter rack will also include an assessment device for assessing the EBL and/or Hb levels of the patient based on the parameters of the used sponge returned to the smart sponge counter rack and the set of instructions stored on the non-transitory computer readable memory will further indicate the EBL and/or Hb levels of the patient based on the assessment device's assessment of the returned used sponge and alert the user if EBL and/or Hb levels raise concern for the wellbeing of the patient.

In addition to the above, disclosed herein is a system and method that collects data from the above identified embodiments. In some forms, this information will be tracked and used to identify what procedures were done well and what procedures could have been done better (e.g., a catalog or database of scanning science to be used and learned from over time). In a preferred form, the data will be used and stored in a database of all such procedures for use in later data mining to help determine best practices and/or practices to avoid (e.g., what scan pattern worked best for a particular procedure, what average scan speed (or pace) did successful procedures follow, what average distance (or proximity) was the wand held at during successful procedures, what wand type has the best results for a particular procedure, was a full body scan conducted or a partial body scan, was a room scan conducted, was a room scan conducted before or after a body scan, what common element existed in procedures that did not go well, what medical items were used in procedures that went well and what ones were used in procedures that did not go well or resulted in a missing item, etc.). In some configurations, the system will provide real-time reporting or feedback to the user indicating the quality of the wanding method being used by the user. The system may also prevent personnel from closing a case or procedure out until proper wand technique is achieved. In preferred forms, the system will work with other medical equipment to prevent such a close out until a proper body scan of the patient and proper room scan was done after the body scan.

As should be evident by the above examples, numerous types of data can be collected with the wand system and this data can equally be used in numerous different ways (some right away such as the real-time feedback example given above, others much later down the road such as the research and education examples given above). As medical equipment makers learn of this available data and its uses, it is contemplated that more and more medical devices will be configured to interface with one another to share this data and utilize it to ensure that all proper steps are taken before a procedure is concluded (or before it can be closed out). In this way, the data may be used to help control workflow for the procedure (e.g., procedural process steps, reporting, notifications, interfaces, etc.) to help improve overall medical procedures. For example, in some configurations this data will recognize problems as they happen and require counteractions to make-up for same, such as requiring the user to restart the entire scanning process if it is detected that the wand was used improperly during the prior scan. This may mean that this is done the moment a single improper usage is detected (e.g., out of scan read range, moving too fast, held in the wrong orientation, etc.), or the system may be configured to do this after a certain number of improper usages are detected. In a preferred form, the number of improper usage detections and types of improper usage will all be part of the data studied over time to perfect exactly what should cause the user to restart the entire scan (e.g., for example, it may be found in conventional knee replacement procedure that being out of read range up to three times is acceptable, but moving over the desired scan speed just once is enough to merit restarting of the entire scan).

The system may also be setup to require the user to provide biometric input or interface before using the wand to utilize this information along with the wand information. For example, the system may be equipped with a fingerprint scanner 131 (FIG. 3) that a user will have to use before operating the system and the system will store that biometric information along with the data collected from the use of the wand for later review and/or use. Alternatively, other biometric data may be required (e.g., face scan, eye scan, voice analysis, etc.). In this way, a party using the wand can be tracked down to confirm who used the device during any portion of the proceeding. This information could also be used to confirm who used the wand, how many people used the wand during a procedure, etc. In a preferred form, the system will require use of the biometric input to log into the system. While the system shows the biometric input being located on display, it should be understood that in alternate configuration the biometric input may be located on the wand 120, the scanner 170, cart 107d, or elsewhere on the system. In some forms, all components may have such a biometric input and require the input prior to the component being used.

In addition to the systems and apparatus discussed herein, it should be understood that numerous methods are also disclosed herein. For example, a method for confirming a scanning device is within a proper read range is disclosed herein. Other methods include methods of manufacturing and/or using an item retention wand are disclosed, as are methods of detecting wands within proper read range, methods for signaling object retention wand positions (e.g., within proper read range, outside of proper read range, at threshold of proper read range, etc.), methods of providing automatic visual, audible and/or haptic feedback to object retention wand users. Similarly, methods of communicating between medical systems are disclosed (e.g., communicating between a sponge counter rack and a reconciliation system; communicating between a sponge counter rack, a reconciliation system and a larger scale object retention system; methods of communicating between a larger scale object retention system and an integrated sponge counter rack and reconciliation system), methods of tracking sponges stored in a sponge counter rack, methods of integrating a sponge counter rack and reconciliation system, methods of placing external antennas for a sponge detector, methods of tracking sponges throughout a medical procedure, methods of automatically checking in sponges used in a medical procedure, methods for detecting EBL and/or Hb levels based on an assessment of a used sponge, etc.

Thus, it should be understood that numerous methods, systems and apparatus are disclosed herein for counting medical procedure objects, reconciling same, estimating patient blood loss during and/or after a procedure, and/or communicating between medical equipment used in a medical procedure setting. More particularly, many systems, methods and apparatus for counting and/or reconciling medical sponges with passive or active tracking devices, properly detecting/estimating blood loss during and/or after a medical procedure to assist with transfusion decision-making and identifying or at least alerting as to post-procedure patient risks, and/or for communicating between devices used during procedures to provide a smart/connected medical procedure environment are disclosed and/or illustrated herein. This detailed description refers to specific examples in the drawings and illustrations. These examples are described in sufficient detail to enable those skilled in the art to practice the inventive subject matter. These examples also serve to illustrate how the inventive subject matter can be applied to various purposes or embodiments. Other embodiments are included within the inventive subject matter, as logical, mechanical, electrical, and other changes can be made to the example embodiments described herein. Features of various embodiments described herein, however essential to the example embodiments in which they are incorporated, do not limit the inventive subject matter as a whole, and any reference to the invention, its elements, operation, and application are not limiting as a whole, but serve only to define these example embodiments. This detailed description does not, therefore, limit embodiments of the invention, which are defined only by the appended claims. Each of the embodiments described herein are contemplated as falling within the inventive subject matter, which is set forth in the following claims. Further, it should be understood that features of one embodiment described herein may be combined with features of other embodiments described herein in order to develop yet further embodiments and such further embodiments are contemplated within this disclosure.

What is claimed is:

1. An integrated sponge counter rack and sponge reconciliation system comprising:
   a base having a plurality of wheels extending below the base for mobilizing the base, and a support extending generally perpendicular to and above the base;
   a sponge bag rack extending from the support for holding at least one sponge bag having a plurality of pockets for receiving used sponges from the plurality of sponges;
   a receptacle coupled to the base and/or support, the receptacle configured to receive individual ones of the used sponges before the used sponges are placed within the plurality of pockets;
   a camera coupled to the base and/or support such that a field of view of the camera includes a portion of the receptacle into which the individual ones of the used sponges are placed, the camera configured to capture images of the individual ones of the used sponges as placed within the portion of the receptacle;
   a sponge detector coupled to the base and/or support, the sponge detector configured to detect the individual ones of the used sponges when placed in the receptacle and generate a respective identifier for each of the individual ones of the used sponges that are detected;

a controller in electrical communication with the camera and the sponge detector, the controller configured to receive the images from the camera and the respective identifier for each of the individual ones of the used sponges that are detected from the sponge detector, wherein the controller is further configured to link the respective identifier for each of the individual ones of the used sponges with a corresponding one of the images; and a display connected to the support or sponge bag rack and in electrical communication with the controller, the display configured to display data relating to the plurality of sponges at the direction of the controller.

2. The integrated sponge counter rack and sponge reconciliation system of claim 1 wherein the plurality of sponges include a marker, wherein the sponge detector includes a scanner configured to detect the marker, and wherein the controller configured to check out the plurality of sponges based on detection of the marker by the scanner prior to the plurality of sponges being used in a medical procedure.

3. The integrated sponge counter rack and sponge reconciliation system of claim 1 wherein the plurality of sponges include a marker for identifying the plurality of sponges and the system further includes a wand removably attachable to the support or sponge rack so that the wand can be removed therefore, the wand configured to scan a target area for any missing sponges from the plurality of sponges prior to close out of a medical procedure.

4. The integrated sponge counter rack and sponge reconciliation system of claim 1 wherein the at least one sponge bag comprises a plurality of sponge bags movable between an initial stored position within a dispensable box and a deployed position, wherein the plurality of sponge bags are folded when in the initial stored position and are unfolded and suspended from the sponge rack to expose the plurality of pockets thereon when in the deployed position, and wherein the sponge bag rack includes a receptacle for receiving the dispensable box so that sponge bags may be dispensed from the box therefrom.

5. An integrated medical procedure room having equipment that communicates with one another comprising:

an object retention system having a controller and a display, the display configured to display data related to objects present for use with a medical procedure;

a wand for scanning a target area to locate retained objects and having a wand communication circuit for communicating real-time data relating to the wand to the object retention system controller for display on the display;

a sponge counter rack or reconciliation system for tracking sponges used during the medical procedure and having a sponge counter rack or reconciliation system communication circuit for communicating real-time data relating to the sponge counter rack or reconciliation system to the object retention system controller for display on the display, wherein the sponge counter rack or reconciliation system is configured to capture images of the sponges with a camera, generate a respective identifier for each of the sponges when detected by a sponge detector, and link the respective identifier for each of the sponges with a corresponding one of the images.

* * * * *